(12) United States Patent
Klimovitch et al.

(10) Patent No.: US 10,549,105 B2
(45) Date of Patent: Feb. 4, 2020

(54) APPARATUSES AND METHODS THAT IMPROVE CONDUCTIVE COMMUNICATION BETWEEN EXTERNAL PROGRAMMERS AND IMPLANTABLE MEDICAL DEVICES

(71) Applicant: Pacesetter, Inc., San Jose, CA (US)

(72) Inventors: Gleb Klimovitch, Santa Clara, CA (US); Timothy Edward Ciciarelli, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 7 days.

(21) Appl. No.: 15/458,656

(22) Filed: Mar. 14, 2017

(65) Prior Publication Data

US 2018/0236249 A1    Aug. 23, 2018

Related U.S. Application Data

(60) Provisional application No. 62/460,510, filed on Feb. 17, 2017.

(51) Int. Cl.
| A61N 1/372 | (2006.01) |
| A61N 1/362 | (2006.01) |
| A61N 1/39 | (2006.01) |
| A61N 1/375 | (2006.01) |

(52) U.S. Cl.
CPC .......... *A61N 1/37217* (2013.01); *A61N 1/362* (2013.01); *A61N 1/3756* (2013.01); *A61N 1/3962* (2013.01)

(58) Field of Classification Search
CPC ............ A61N 1/37217; A61N 1/37235; A61N 1/362; A61N 1/3756; A61N 1/3962; H04B 13/005
See application file for complete search history.

(56) References Cited

U.S. PATENT DOCUMENTS

| 8,788,053 B2 | 7/2014 | Jacobson |
| 2016/0121127 A1 | 5/2016 | Klimovitch et al. |
| 2016/0121129 A1 | 5/2016 | Persson et al. |
| 2016/0250483 A1 | 9/2016 | Klimovitch et al. |

*Primary Examiner* — Lindsey G Wehrheim
(74) *Attorney, Agent, or Firm* — Theresa A. Raymer

(57) ABSTRACT

Described herein are apparatuses and methods that improve conductive communication between an external programmer and an implantable medical device (IMD) that is implanted within a patient. In an embodiment, an auxiliary apparatus of the present technology includes a first auxiliary skin electrode configured to attach to skin of a patient, a second auxiliary skin electrode configured to attach to skin of a patient, and an electrically conductive path extending between the first and second auxiliary skin electrodes and interrupted by a capacitor. The auxiliary apparatus is distinct from the external programmer and the IMD, and can beneficially be used to improve conductive communication therebetween without making any modifications to the external programmer, and without making any modifications to the IMD.

20 Claims, 10 Drawing Sheets

APPARATUSES AND METHODS THAT IMPROVE CONDUCTIVE COMMUNICATION BETWEEN EXTERNAL PROGRAMMERS AND IMPLANTABLE MEDICAL DEVICES

PRIORITY

The present application relates to and claims priority from U.S. provisional application Ser. No. 62/460,510, filed Feb. 17, 2017, entitled "Apparatuses and Methods That Improve Conductive Communication Between External Programmers And Implantable Medical Devices," which is hereby expressly incorporated by reference in its entirety to provide continuity of disclosure.

FIELD OF TECHNOLOGY

Embodiments described herein generally relate to apparatuses and methods for improving conductive communication between non-implantable devices, such as external programmers, and implantable medical devices (IMDs), such as leadless pacemakers (LPs).

BACKGROUND

Communication between the one or more implantable medical devices (IMDs) and an external programmer may be facilitated by conductive communication via patient tissue. The use of conductive communication of information provides certain improvements over more conventional communication techniques. For example, conductive communication techniques enable communication without requiring a programmer head be held undesirably close to a patient or to be held in a precise position relative to an implant site for an extended period of time. Conductive communication also enables power consumption to be reduced due to substantially lower current requirements and eliminating peak power demands currently imposed by existing inductive and radio frequency (RF) communication techniques. This can beneficially extend the life of an IMD. Also, conductive communication techniques use elements generally already existing in an IMD, such as the therapeutic electrodes that function as an input-output device, enabling elimination of a coil or antenna that are conventionally used for inductive and RF communication and reducing complexity and component count significantly.

In order to perform conductive communication, at least two programmer skin electrodes (that are part of or coupled to an external programmer) are attached to skin of a patient in whom one or more IMDs is/are implanted, and the programmer skin electrodes are used to transmit information to and/or receive information from the IMD(s) via conduction through body tissue of the patient. One potential problem with using conductive communication is that the orientation of the IMD(s) can cause fading that can adversely affect both programmer-to-implant (p2i) communication and implant-to-programmer (i2p) communication. More specifically, certain orientations of an IMD may cause conductive communication to be intermittent or stop completely, which may occur when an electric potential field generated between programmer skin electrodes has too small a difference between the electrodes of the IMD. It is often impractical to mitigate such fading by changing the orientation of an IMD and/or the placement of its electrodes, since the orientation of the IMD and/or the placement of its electrodes is already severely constrained by mechanical requirements and implant-to-implant (i2i) communication requirements. Further, where the programmer skin electrodes are also being used to sense an electrocardiogram (ECG), which is often the case, it may be impractical to mitigate such fading by changing the placement of the programmer skin electrodes since the placement of such electrodes is often fixed or at least constrained by ECG requirements.

SUMMARY

Embodiments of the present technology relate to apparatuses and methods that improve conductive communication between an external programmer and one or more IMDs that is/are implanted within a patient. In an embodiment, an auxiliary apparatus of the present technology includes a first auxiliary skin electrode configured to attach to skin of a patient, a second auxiliary skin electrode configured to attach to skin of a patient, and an electrically conductive path that extends between the first and second auxiliary skin electrodes and is interrupted by a capacitor. The auxiliary apparatus is distinct from the external programmer and the IMD(s), and can beneficially be used to improve conductive communication there between without making any modifications to the external programmer, and without making any modifications to the IMD.

An IMD with which embodiments of the present technology can be used includes or is coupled to at least two implantable electrodes that enable the IMD to at least one of transmit information to or receive information from the external programmer via conduction through body tissue of the patient. An external programmer with which embodiments of the present technology can be used includes or is coupled to at least two programmer skin electrodes that are configured to attach to skin of the patient and that enable the external programmer to at least one of transmit information to or receive information from the IMD via conduction through body tissue of the patient. An electric field vector is generated between a pair of the at least two programmer skin electrodes when the external programmer uses the pair to transmit information to or receive information from the IMD via conduction through body tissue. An auxiliary apparatus of the present technology can be used to modify a direction of the electric field vector generated between the pair of the at least two programmer skin electrodes to thereby improve the conductive communication between the external programmer and the IMD. The auxiliary apparatus of the present technology can also cause a phase shift in communication signals that travel via conduction through body tissue to thereby reduce a probability and a depth of fading that may occur in the communication signals that travel via conduction through body tissue.

In accordance with certain embodiments, the auxiliary apparatus only includes passive components, i.e., does not include any active components. For example, in accordance with certain embodiments, the auxiliary apparatus simply includes the pair of auxiliary skin electrodes, electrically conductive wires and a capacitor that interrupts that electrically conductive path between the auxiliary skin electrodes provided by the wires. In accordance with an embodiment, the capacitor passes frequencies within a first frequency band used for the conductive communication between the external programmer and IMD, and the capacitor attenuates frequencies within a second frequency band that is lower than the first frequency band and in which cardiac electrical activity occurs. Accordingly, the capacitor of the auxiliary apparatus does not adversely affect the external programmer's ability to sense ECG signals using the at least two programmer skin electrodes.

In accordance with certain embodiments, the auxiliary apparatus includes an inductor in series with the capacitor. The inductor and the capacitor collectively provide a series resonant LC band-pass filter that is configured to pass electric currents in a first frequency band used for the conductive communication between the external programmer and IMD, and attenuate electric currents at frequencies outside of the first frequency band, e.g., which include ECG content.

As noted above, in accordance with certain embodiments the auxiliary apparatus does not include any active electrical components, and thus, does not require its own power supply. In accordance with alternative embodiments, an auxiliary apparatus includes one or more active electrical components.

Certain embodiments of the present technology, as noted above, are directed to methods for improving conductive communication between an external programmer and one or more IMD(s) that is/are implanted within a patient. Such an IMD includes or is coupled to at least two implantable electrodes that enable the IMD to at least one of transmit information to or receive information from the external programmer via conduction through body tissue of the patient. In accordance with an embodiment, a method includes attaching at least two programmer skin electrodes to different skin locations on the patient, wherein the at least two programmer skin electrodes are part of or electrically coupled to the external programmer. The method also includes attaching first and second auxiliary skin electrodes of an auxiliary apparatus to different skin locations on the patient, wherein the auxiliary apparatus also includes an electrically conductive path extending between the first and second auxiliary skin electrodes and interrupted by a capacitor. The auxiliary apparatus is distinct from (i.e., not part of) the external programmer and the IMD. The method further includes using the auxiliary apparatus to modify a direction of an electric field vector generated between the at least two programmer skin electrodes to thereby improve the conductive communication between the external programmer and the IMD. The method can also include using the auxiliary apparatus to cause a phase shift in communication signals that travel via conduction through body tissue of the patient and thereby reduce a probability and a depth of fading that may occur in the communication signals that travel via conduction through body tissue of the patient.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

BRIEF DESCRIPTION OF THE DRAWINGS

Embodiments of the present technology relating to both structure and method of operation may best be understood by referring to the following description and accompanying drawings, in which similar reference characters denote similar elements throughout the several views.

DETAILED DESCRIPTION

Embodiments of the present technology relate to apparatuses and methods that improve conductive communication between an external programmer and one or more implantable medical devices (IMDs) that is/are implanted within a patient. An example of such an IMD is a leadless cardiac pacemaker, which can also be referred to more succinctly as a leadless pacemaker (LP). Another example of an IMD is an implantable cardiac defibrillator (ICD), such as a subcutaneous-ICD (S-ICD). Before providing addition details of the specific embodiments of the present technology mentioned above, an exemplary system in which embodiments of the present technology can be used will first be described with reference to FIGS. 1-5. More specifically, FIGS. 1-5 will be used to describe an exemplary cardiac pacing system, wherein pacing and sensing operations can be performed by multiple medical devices, which may include one or more LPs, an ICD, such as an S-ICD, and/or an external programmer that reliably and safely coordinates pacing and/or sensing operations.

Figure 1:
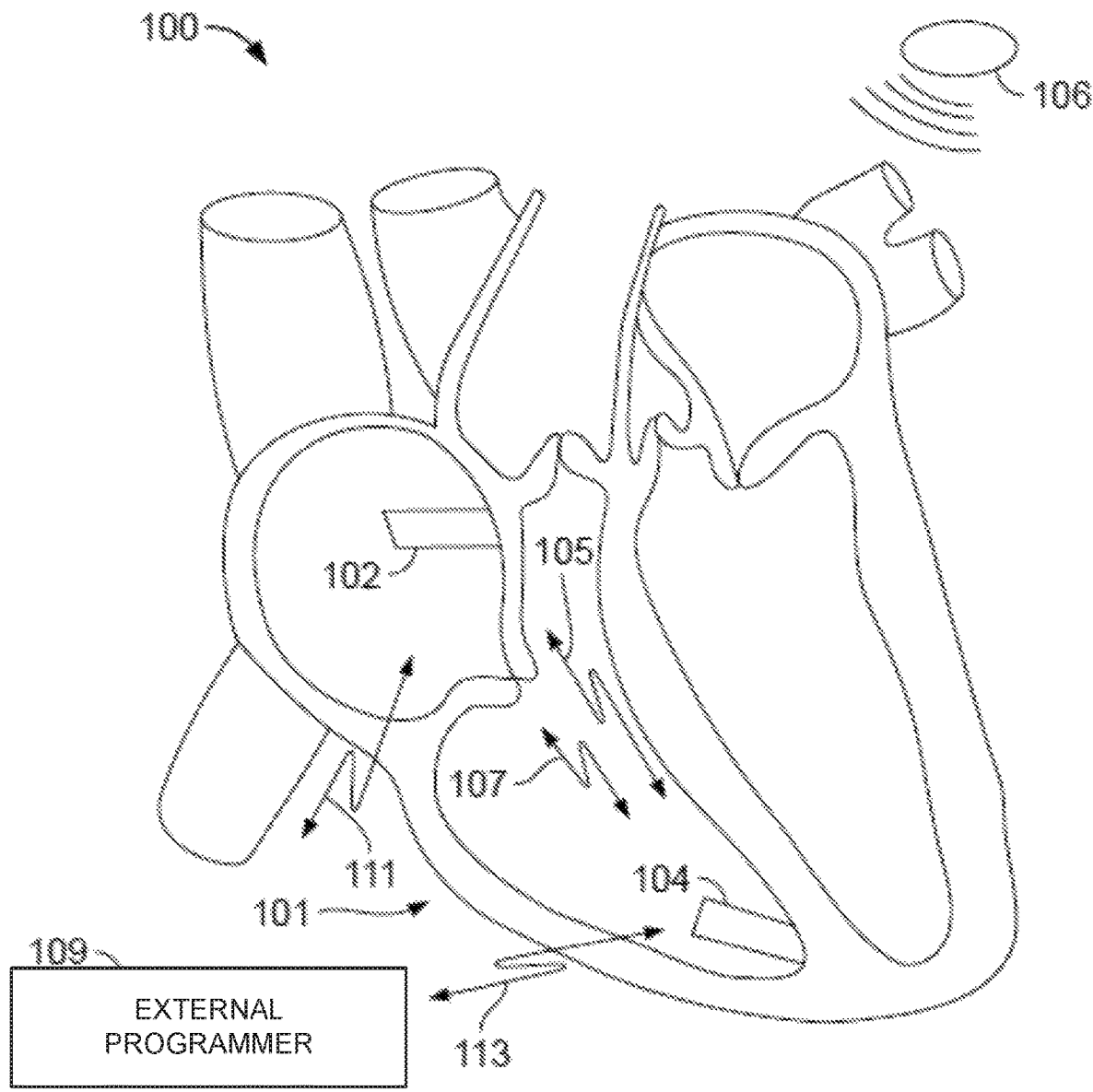
FIG. 1 illustrates a portion of system formed in accordance with certain embodiments herein as implanted in a heart.

FIG. 1 illustrates a cardiac pacing system 100 that is configured to be implanted in a heart 101. The cardiac pacing system 100 comprises two or more LPs 102 and 104 located in different chambers of the heart. LP 102 is located in a right atrium, while LP 104 is located in a right ventricle. LPs 102 and 104 communicate with one another to inform one another of various local physiologic activities, such as local intrinsic events, local paced events and the like. LPs 102 and 104 may be constructed in a similar manner, but operate differently based upon which chamber LP 102 or 104 is located.

In some embodiments, LPs 102 and 104 communicate with one another, with an ICD 106, and with an external device (programmer) 109 through wireless transceivers, communication coils and antenna, and/or more preferably by conductive communication through the same electrodes as used for sensing and/or delivery of pacing therapy. When conductive communication is maintained through the same electrodes as used for pacing, the cardiac pacing system 100 may omit an antenna or telemetry coil in one or more of LPs 102 and 104.

In some embodiments, one or more LPs 102 and 104 can be co-implanted with the ICD 106. Each LP 102, 104 uses two or more electrodes located within, on, or within a few centimeters of the housing of the LP, for pacing and sensing at the cardiac chamber, for bidirectional communication with one another, with the external programmer 109, and the ICD 106.

Exemplary Leadless Pacemaker

Figure 2:
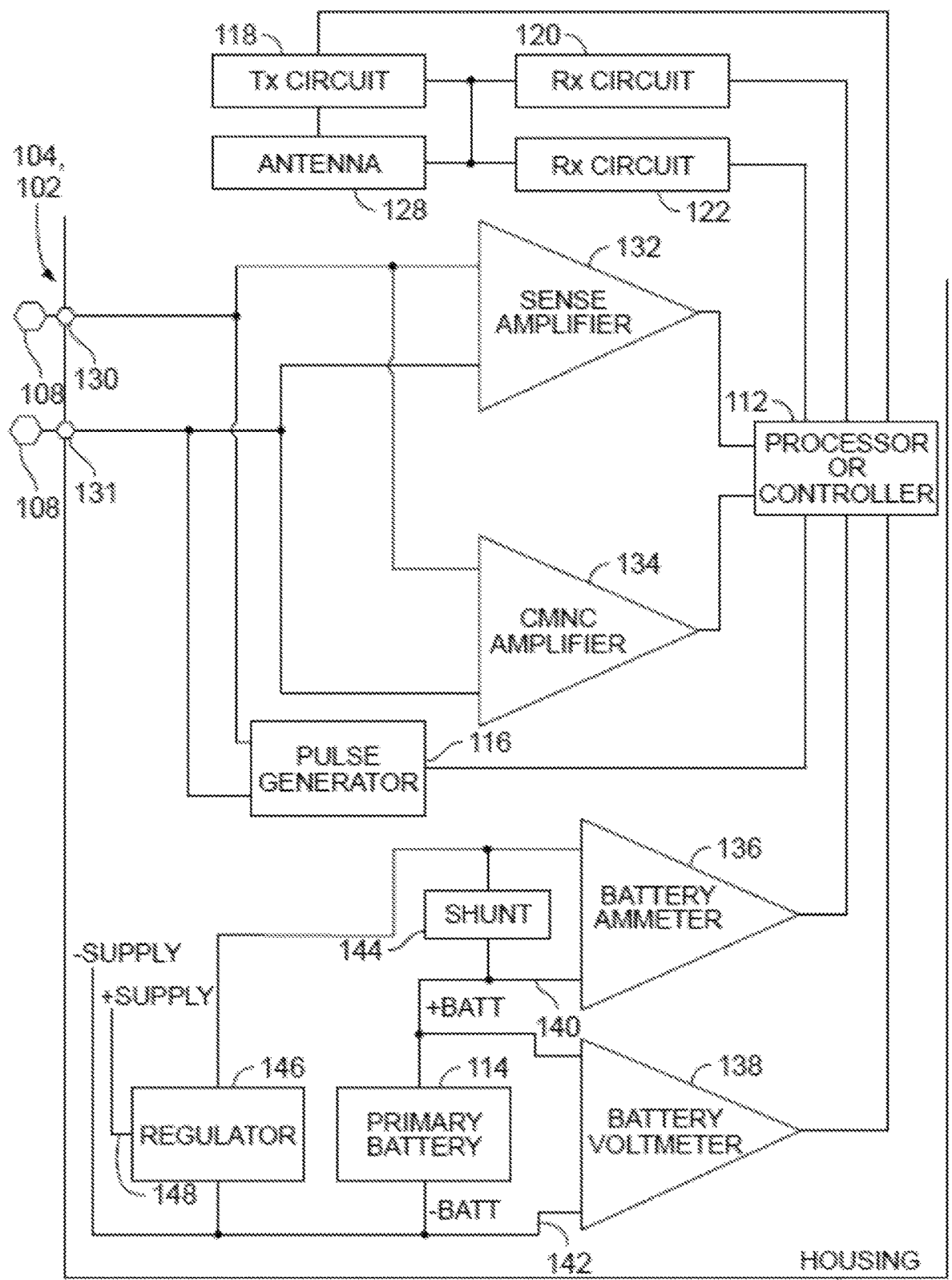
FIG. 2 is a block diagram of a single LP in accordance with certain embodiments herein.

Referring to FIG. 2, a pictorial diagram shows an embodiment for portions of the electronics within LP 102, 104 configured to provide conductive communication through the sensing/pacing electrodes. One or more of LPs 102 and 104 comprise at least two leadless electrodes 108 configured for delivering cardiac pacing pulses, sensing evoked and/or natural cardiac electrical signals, and uni-directional or bi-directional communication.

LP 102, 104 includes a transmitter 118 and first and second receivers 120 and 122 that collectively define separate first and second communication channels 105 and 107 (FIG. 1), (among other things) between LPs 102 and 104. Although first and second receivers 120 and 122 are depicted, in other embodiments, LP 102, 104 may only include first receiver 120, or may include additional receivers other than first and second receivers 120 and 122. LP 102, 104 may only also include one or more transmitters in addition to transmitter 118. In certain embodiments, LPs 102 and 104 may communicate over more than just first and second communication channels 105 and 107. In certain embodiments, LPs 102 and 104 may communicate over one common communication channel 105. The transmitter 118 and receiver(s) 120, 122 may each utilize a separate antenna or may utilize a common antenna 128. In accordance with specific embodiments, LPs 102 and 104 communicate conductively over a common physical channel via the same electrodes 108 that are also used to deliver pacing pulses. Usage of the electrodes 108 for communication enables the one or more LPs 102 and 104 to perform antenna-less and telemetry coil-less communication. Where conductive communication is employed, the antenna(s) 128 can be eliminated, thereby reducing complexity and component count of the LPs 102 and 104. Further, where conductive communication is employed, there is no need for any inductive coil(s) that are used for telemetry.

In accordance with certain embodiments, when LP 102, 104 senses an intrinsic event or delivers a paced event, the corresponding LP 102, 104 transmits an implant event message to the other LP 102, 104. For example, when an atrial LP 102 senses/paces an atrial event, the atrial LP 102 transmits an implant event message including an event marker indicative of a nature of the event (e.g., intrinsic/sensed atrial event, paced atrial event). When a ventricular LP 104 senses/paces a ventricular event, the ventricular LP 104 transmits an implant event message including an event marker indicative of a nature of the event (e.g., intrinsic/sensed ventricular event, paced ventricular event). In certain embodiments, LP 102, 104 transmits an implant event message to the other LP 102, 104 preceding the actual pace pulse so that the remote LP can blank its sense inputs in anticipation of that remote pace pulse (to prevent inappropriate crosstalk sensing).

The implant event messages may be formatted in various manners. As one example, each event message may include a leading trigger pulse (also referred to as an LP wakeup notice or wakeup pulse) followed by an event marker. The notice trigger pulse is transmitted over a first channel (e.g., with a pulse duration of approximately 10 µs to approximately 1 ms and/or within a fundamental frequency range of approximately 1 kHz to approximately 100 kHz). The notice trigger pulse indicates that an event marker is about to be transmitted over a second channel (e.g., within a higher frequency range). The event marker can then be transmitted over the second channel.

The event markers may include data indicative of one or more events (e.g., a sensed intrinsic atrial activation for an atrial located LP, a sensed intrinsic ventricular activation for a ventricular located LP). The event markers may include different markers for intrinsic and paced events. The event markers may also indicate start or end times for timers (e.g., an AV interval, a blanking interval, etc.). Optionally, the implant event message may include a message segment that includes additional/secondary information.

Optionally, the LP (or other IMD) that receives any implant-to-implant (i2i) communication from another LP (or other IMD) or from an external device may transmit a receive acknowledgement indicating that the receiving LP/IMD received the i2i communication, etc.

The event messages enable the LPs 102, 104 to deliver synchronized therapy and additional supportive features (e.g., measurements, etc.). To maintain synchronous therapy, each of the LPs 102 and 104 is made aware (through the event messages) when an event occurs in the chamber containing the other LP 102, 104. Some embodiments described herein provide efficient and reliable processes to maintain synchronization between LPs 102 and 104 without maintaining continuous communication between LPs 102 and 104. In accordance with certain embodiments herein, the transmitter(s) 118 and receiver(s) 120, 122 utilize low power event messages/signaling between multiple LPs 102 and 104. The low power event messages/signaling may be maintained between LPs 102 and 104 synchronously or asynchronously.

For synchronous event signaling, LPs 102 and 104 maintain synchronization and regularly communicate at a specific interval. Synchronous event signaling allows the transmitter and receivers in each LP 102,104 to use limited (or minimal) power as each LP 102, 104 is only powered for a small fraction of the time in connection with transmission and reception. For example, LP 102, 104 may transmit/receive (Tx/Rx) communication in time slots having duration of 10-20 µs, where the Tx/Rx time slots occur periodically (e.g., every 10-20 ms). In the foregoing example, a receiver 120, 122 that is active/ON (also referred to as awake) for select receive time slots, that are spaced apart several milliseconds, may draw an amount of current that is several times less (e.g., 1000× less) than a current draw of a receiver that is "always on" (always awake).

LPs 102 and 104 may lose synchronization, even in a synchronous event signaling scheme. As explained herein, features may be included in LPs 102 and 104 to maintain device synchronization, and when synchronization is lost, LPs 102 and 104 undergo operations to recover synchronization. Also, synchronous event messages/signaling may introduce a delay between transmissions which causes a reaction lag at the receiving LP 102, 104. Accordingly, features may be implemented to account for the reaction lag.

During asynchronous event signaling, LPs 102 and 104 do not maintain communication synchronization. During asynchronous event signaling, one or more of receivers 120 and 122 of LPs 102 and 104 may be "always on" (always awake) to search for incoming transmissions. However, maintaining LP receivers 120, 122 in an "always on" (always awake) state presents challenges as the received signal level often is low due to high channel attenuation caused by the patient's anatomy. Further, maintaining the receivers awake will deplete the battery 114 more quickly than may be desirable.

The asynchronous event signaling methods avoid risks associated with losing synchronization between devices. However, the asynchronous event signaling methods utilize additional receiver current between transmissions. For purposes of illustration only, a non-limiting example is described hereafter. For example, the channel attenuation may be estimated to have a gain of 1/500 to 1/10000. A gain factor may be 1/1000th. Transmit current is a design factor in addition to receiver current. As an example, the system may allocate one-half of the implant communication current budget to the transmitter (e.g., 0.5 µA for each transmitter). When LP 102, 104 maintains a transmitter in a continuous on-state and the electrode load is 500 ohms, a transmitted voltage may be 0.250 mV. When an event signal is transmitted at 0.250 mV, the event signal is attenuated as it propagates and would appear at LP 102, 104 receiver as an amplitude of approximately 0.25 µV. The receivers 120 and 122 can utilize a synchronization threshold to help differentiate incoming communication signals from noise. As an example, the synchronization threshold may be 0.5 µV (or more generally 0.25 µV to 5 µV), which would cause LP 102, 104 receiver to reject an incoming communication signal that exhibits a receive voltage below 0.5 µV. Nevertheless, even with the use of the synchronization threshold, noise may still be mistaken as being communication signals, and more specifically, as being messages.

To overcome the foregoing receive power limit, a pulsed transmission scheme may be utilized in which communication transmissions occur correlated with an event. By way of example, the pulsed transmission scheme may be simplified such that each transmission constitutes a single pulse of a select amplitude and width.

When LP transmitter 118 transmits event signals over a conductive communication channel that has an electrode load of 500 ohm using a 1 ms pulse width at 2.5 V at a rate of 60 bpm, LP transmitter 118 will draw 4.4 µA for transmit current. When LP transmitter 118 transmits event signals at 2.5 V using a 2 µs pulse width, transmitter 118 only draws 10 nA to transmit event messages at a rate of 60 bpm. In order to sense an event message (transmitted with the foregoing parameters), receivers 120 and 122 may utilize 50 µA. In accordance with certain embodiments herein, the pulse widths and other transmit/receive parameters may be adjusted to achieve a desired total (summed) current demand from both transmitter 118 and receivers 120 and 122. The transmitter current decreases nearly linearly with narrowing bandwidth (pulse width), while a relation between receiver current and bandwidth is non-linear.

In accordance with certain embodiments herein, LPs 102 and 104 may utilize multi-stage receivers that implement a staged receiver wakeup scheme in order to improve reliability yet remain power efficient. Each of LPs 102 and 104 may include first and second receivers 120 and 122 that operate with different first and second activation protocols and different first and second receive channels. For example, first receiver 120 may be assigned a first activation protocol that is "always on" (also referred to as always awake) and that listens over a first receive channel that has a lower fundamental frequency range/pulse duration (e.g., 1 kHz to 100 kHz/10 µs to approximately 1 ms) as compared to the fundamental frequency range (e.g., greater than 100 kHz/less than 10 µs per pulse) assigned to the second receive channel. First receiver 120 may maintain the first channel active (awake) for at least a portion of a time when the second channel is inactive (asleep) to listen for event messages from a remote LP. The controller or processor determines whether the incoming signal received over the first channel corresponds to an LP wakeup notice. The second receiver 122 may be assigned a second activation protocol that is a triggered protocol, in which the second receiver 122 becomes active (awake) in response to detection of trigger events over the first receive channel (e.g., when the incoming signal corresponds to the LP wakeup notice, activating the second channel at the local LP).

The marker message may represent a signature indicative of an event qualification to qualify a valid event marker pulse. The event qualification messages distinguish a message from spurious noise and avoid mistaking other signals as event messages having implant markers. The event message may be repeated to allow the LP receiver 120 multiple chances to "catch" the event qualification. Additionally or alternatively, the Tx and Rx LP 102, 104 may implement a handshaking protocol in which the Tx and Rx LP 102, 104 exchange additional information, such as to allow a response to follow the marker. The exchange of additional information may be limited or avoided in certain instances as the exchange draws additional power when sending and receiving the information. Optionally, the event message may be configured with additional content to provide a more robust event marker.

Transmitter 118 may be configured to transmit the event messages in a manner that does not inadvertently capture the heart in the chamber where LP 102, 104 is located, such as when the associated chamber is not in a refractory state. In addition, an LP 102, 104 that receives an event message may enter an "event refractory" state (or event blanking state) following receipt of the event message. The event refractory/blanking state may be set to extend for a determined period of time after receipt of an event message in order to avoid the receiving LP 102, 104 from inadvertently sensing another signal as an event message that might otherwise cause retriggering. For example, the receiving LP 102, 104 may detect a measurement pulse from another LP 102, 104 or programmer 109.

In accordance with certain embodiments herein, programmer 109 may communicate over a programmer-to-LP channel, 111 (FIG. 1) with LP 102, 104 utilizing the same communication scheme. The external programmer may listen to the event message transmitted between LP 102, 104 and synchronize programmer to implant communication such that programmer 109 does not transmit communication signals 113 until after an implant-to-implant (i2i) messaging sequence is completed. The programmer-to-LP channel may be referred to more generally as the programmer-to-implant channel, and the communication therebetween can be referred to more generally as programmer-to-implant (p2i) and implant-to-programmer (i2p) communication.

In accordance with certain embodiments, LP 102, 104 may combine transmit operations with therapy. The transmit event marker may be configured to have similar characteristics in amplitude and pulse width to a pacing pulse and LP 102, 104 may use the energy in the event messages to help capture the heart. For example, a pacing pulse may normally be delivered with pacing parameters of 2.5 V amplitude, 500 ohm impedance, 60 bpm pacing rate, 0.4 ms pulse width. The foregoing pacing parameters correspond to a current draw of about 1.9 µA. The same LP 102, 104 may implement an event message utilizing event signaling parameters for amplitude, pulse width, pulse rate, etc. that correspond to a current draw of approximately 0.5 µA for transmit.

LP 102, 104 may combine the event message transmissions with pacing pulses. For example, LP 102, 104 may use a 50 µs wakeup transmit pulse having an amplitude of 2.5 V which would draw 250 nC (nano Coulombs) for an electrode load of 500 ohm. The pulses of the transmit event message may be followed by an event message encoded with a sequence of short duration pulses (for example 16, 2 µs on/off bits) which would draw an additional 80 nC. The event message pulse would then be followed by the remaining pulse width needed to reach an equivalent charge of a nominal 0.4 ms pace pulse. In this case, the current necessary to transmit the marker is essentially free as it was used to achieve the necessary pace capture anyhow. With this method, the savings in transmit current could be budgeted for the receiver or would allow for additional longevity.

When LP 102, 104 senses an intrinsic event, the transmitter sends a qualitatively similar event pulse sequence (but indicative of a sensed event) without adding the pace pulse remainder. As LP 102, 104 longevity calculations are designed based on the assumption that LP 102, 104 will deliver pacing therapy 100% of the time, transmitting an intrinsic event marker to another LP 102, 104 will not impact the nominal calculated LP longevity.

In some embodiments, LP 102, 104 may deliver pacing pulses at relatively low amplitude. When low amplitude pacing pulses are used, the power budget for event messages may be modified to be a larger portion of the overall device energy budget. As the pacing pulse amplitude is lowered closer to amplitude of event messages, LP 102, 104 increases an extent to which LP 102, 104 uses the event messages as part of the pacing therapy (also referred to as sharing "capture charge" and "transmit charge"). As an example, if the nominal pacing voltage can be lowered to <1.25 V, then a "supply halving" pacing charge circuit could reduce the battery current draw by approximately 50%. A 1.25 V pace pulse would save 1.5 µA of pacing current budget. With lower pulse amplitudes, LP 102, 104 may use larger pulse widths.

By combining event messages and low power pacing, LP 102, 104 may realize additional longevity. Today longevity standards provide that the longevity to be specified based on a therapy that utilizes 2.5 V amplitude, 0.4 ms pulses at 100% pacing. Optionally, a new standard may be established based on pacing pulses that deliver lower amplitude and/or shorter pacing pulses.

In an embodiment, a communication capacitor is provided in LP 102, 104. The communication capacitor may be used to transmit event signals having higher voltage for the event message pulses to improve communication, such as when the LPs 102 and 104 experience difficulty sensing event messages. The high voltage event signaling may be used for implants with high signal attenuation or in the case of a retry for an ARQ (automatic repeat request) handshaking scheme.

For example, when an LP 102, 104 does not receive an event message within a select time out interval, LP 102, 104 may resend an event message at a higher amplitude. As another example, LP 102, 104 may perform an event signaling auto-level search wherein the LPs send event messages at progressively higher amplitude until receiving confirmation that an event message was received (or receiving a subsequent event message from another LP). For example, in DDD mode when the atrial or ventricular LP 102, 104 does not see an event signal from LP 102, 104 in the other chamber before its timeout interval it could automatically raise the amplitude of the event message, until the LPs 102 and 104 become and remain in sync. Optionally, LP 102, 104 may implement a search hysteresis algorithm similar to those used for rate and amplitude capture to allow the lowest safe detectible amplitude to be determined.

The LPs 102 and 104 may be programmable such as to afford flexibility in adjusting the event marker pulse width. In some embodiments, different receiver circuits may be provided and selected for certain pulse widths, where multiple receivers may be provided on a common ASIC, thereby allowing the user to vary the parameters in an LP after implant.

In some embodiments, the individual LP 102 can comprise a hermetic housing 110 configured for placement on or attachment to the inside or outside of a cardiac chamber and at least two leadless electrodes 108 proximal to the housing 110 and configured for bidirectional communication with at least one other device 106 within or outside the body.

FIG. 2 depicts a single LP 102 and shows the LP's functional elements substantially enclosed in a hermetic housing 110. The LP 102 has at least two electrodes 108 located within, on, or near the housing 110, for delivering pacing pulses to and sensing electrical activity from the muscle of the cardiac chamber, and for bidirectional communication with at least one other device within or outside the body. Hermetic feedthroughs 130, 131 conduct electrode signals through the housing 110. The housing 110 contains a primary battery 114 to supply power for pacing, sensing, and communication. The housing 110 also contains circuits 132 for sensing cardiac activity from the electrodes 108, circuits 134 for receiving information from at least one other device via the electrodes 108, and a pulse generator 116 for generating pacing pulses for delivery via the electrodes 108 and also for transmitting information to at least one other device via the electrodes 108. The housing 110 can further contain circuits for monitoring device health, for example a battery current monitor 136 and a battery voltage monitor 138, and can contain circuits for controlling operations in a predetermined manner.

Additionally or alternatively, one or more leadless electrodes 108 can be configured to communicate bidirectionally among the multiple LPs and/or the implanted ICD 106 to coordinate pacing pulse delivery and optionally other therapeutic or diagnostic features using messages that identify an event at an individual pacemaker originating the message and a pacemaker receiving the message react as directed by the message depending on the origin of the message. An LP 102, 104 that receives the event message reacts as directed by the event message depending on the message origin or location. In some embodiments or conditions, the two or more leadless electrodes 108 can be configured to communicate bidirectionally among the one or more LPs 102 and/or the ICD 106 and transmit data including designated codes for events detected or created by an individual pacemaker. Individual pacemakers can be configured to issue a unique code corresponding to an event type and a location of the sending pacemaker.

In some embodiments, an individual LP 102, 104 can be configured to deliver a pacing pulse with an event message encoded therein, with a code assigned according to pacemaker location and configured to transmit a message to one or more other LPs via the event message coded pacing pulse. The pacemaker or pacemakers receiving the message are adapted to respond to the message in a predetermined manner depending on type and location of the event.

Moreover, information communicated on the incoming channel can also include an event message from another LP signifying that the other LP has sensed a heartbeat or has delivered a pacing pulse, and identifies the location of the other pacemaker. For example, LP 104 may receive and relay an event message from LP 102 to the programmer. Similarly, information communicated on the outgoing channel can also include a message to another LP or pacemakers, or to the ICD, that the sending LP has sensed a heartbeat or has delivered a pacing pulse at the location of the sending pacemaker.

Referring again to FIGS. 1 and 2, the cardiac pacing system 100 may comprise an implantable cardioverter-defibrillator (ICD) 106 in addition to LP 102, 104 configured for implantation in electrical contact with a cardiac chamber and for performing cardiac rhythm management functions in combination with the implantable ICD 106. The implantable ICD 106 and the one or more LPs 102, 104 configured for leadless intercommunication by information conduction through body tissue and/or wireless transmission between transmitters and receivers in accordance with the discussed herein.

In a further embodiment, a cardiac pacing system 100 comprises at least one LP 102, 104 configured for implantation in electrical contact with a cardiac chamber and configured to perform cardiac pacing functions in combination with the co-implanted ICD 106. Each LP 102, 104 comprises at least two leadless electrodes 108 configured for delivering cardiac pacing pulses, sensing evoked and/or natural cardiac electrical signals, and transmitting information to the co-implanted ICD 106.

LP 102, 104 can be configured for operation in a particular location and a particular functionality at manufacture and/or at programming by an external programmer. Bidirectional communication among the multiple LPs can be arranged to communicate notification of a sensed heartbeat or delivered pacing pulse event and encoding type and location of the event to another implanted pacemaker or pacemakers. LP 102, 104 receiving the communication decode the information and respond depending on location of the receiving pacemaker and predetermined system functionality.

Also shown in FIG. 2, the primary battery 114 has positive terminal 140 and negative terminal 142. Current from the positive terminal 140 of primary battery 114 flows through a shunt 144 to a regulator circuit 146 to create a positive voltage supply 148 suitable for powering the remaining circuitry of the pacemaker 102. The shunt 144 enables the battery current monitor 136 to provide the processor 112 with an indication of battery current drain and indirectly of device health. The illustrative power supply can be a primary battery 114.

In various embodiments, LP 102, 104 can manage power consumption to draw limited power from the battery, thereby reducing device volume. Each circuit in the system can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit is throttled to recharge the tank capacitor at constant power from the battery.

In some embodiments, the controller 112 in one LP 102 or 104 can access signals on the electrodes 108 and can examine output pulse duration from another pacemaker for usage as a signature for determining triggering information validity and, for a signature arriving within predetermined limits, activating delivery of a pacing pulse following a predetermined delay of zero or more milliseconds. The predetermined delay can be preset at manufacture, programmed via an external programmer, or determined by adaptive monitoring to facilitate recognition of the triggering signal and discriminating the triggering signal from noise. In some embodiments or in some conditions, the controller 112 can examine output pulse waveform from another LP for usage as a signature for determining triggering information validity and, for a signature arriving within predetermined limits, activating delivery of a pacing pulse following a predetermined delay of zero or more milliseconds.

Figure 3:
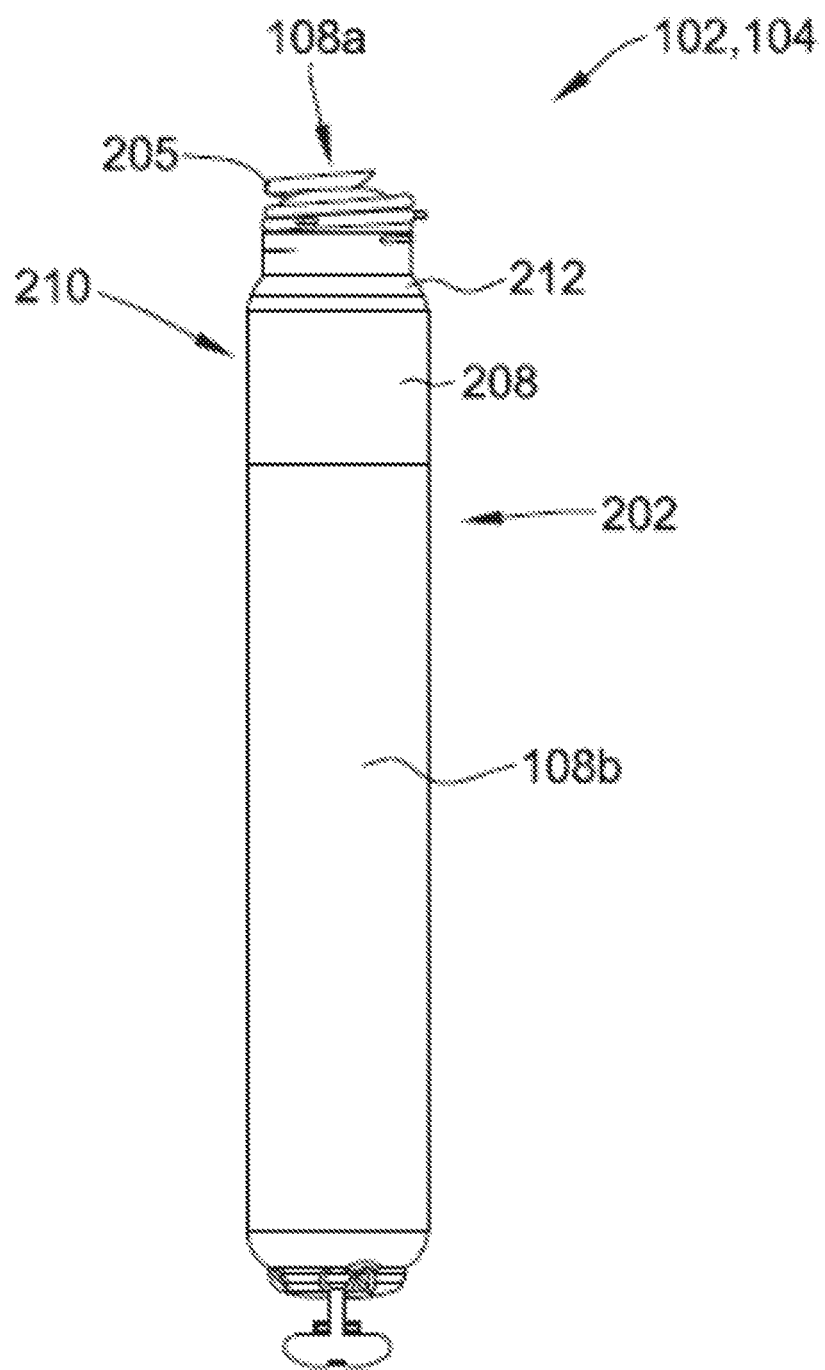
FIG. 3 illustrates an LP in accordance with certain embodiments herein.

FIG. 3 shows an LP 102, 104. The LP can include a hermetic housing 202 with electrodes 108a and 108b disposed thereon. As shown, electrode 108a can be separated from but surrounded partially by a fixation mechanism 205, and the electrode 108b can be disposed on the housing 202. The fixation mechanism 205 can be a fixation helix, a plurality of hooks, barbs, or other attaching features configured to attach the pacemaker to tissue, such as heart tissue.

The housing can also include an electronics compartment 210 within the housing that contains the electronic components necessary for operation of the pacemaker, including, for example, a pulse generator, communication electronics, a battery, and a processor for operation. The hermetic housing 202 can be adapted to be implanted on or in a human heart, and can be cylindrically shaped, rectangular, spherical, or any other appropriate shapes, for example.

The housing can comprise a conductive, biocompatible, inert, and anodically safe material such as titanium, 316L stainless steel, or other similar materials. The housing can further comprise an insulator disposed on the conductive material to separate electrodes 108a and 108b. The insulator can be an insulative coating on a portion of the housing between the electrodes, and can comprise materials such as silicone, polyurethane, parylene, or another biocompatible electrical insulator commonly used for implantable medical devices. In the embodiment of FIG. 3, a single insulator 208 is disposed along the portion of the housing between electrodes 108a and 108b. In some embodiments, the housing itself can comprise an insulator instead of a conductor, such as an alumina ceramic or other similar materials, and the electrodes can be disposed upon the housing.

As shown in FIG. 3, the LP 102, 104 can further include a header assembly 212 to isolate 108a and 108b. The header assembly 212 can be made from PEEK, tecothane or another biocompatible plastic, and can contain a ceramic to metal feedthrough, a glass to metal feedthrough, or other appropriate feedthrough insulator as known in the art.

The electrodes 108a and 108b can comprise pace/sense electrodes, or return electrodes. A low-polarization coating can be applied to the electrodes, such as sintered platinum, platinum-iridium, iridium, iridium-oxide, titanium-nitride, carbon, or other materials commonly used to reduce polarization effects, for example. In FIG. 3, electrode 108a can be a pace/sense electrode and electrode 108b can be a return electrode. The electrode 108b can be a portion of the conductive housing 202 that does not include an insulator 208.

Several techniques and structures can be used for attaching the housing 202 to the interior or exterior wall of the heart. A helical fixation mechanism 205, can enable insertion of the device endocardially or epicardially through a guiding catheter. A torqueable catheter can be used to rotate the housing and force the fixation device into heart tissue, thus affixing the fixation device (and also the electrode 108a in FIG. 3) into contact with stimulable tissue. Electrode 108b can serve as an indifferent electrode for sensing and pacing. The fixation mechanism may be coated partially or in full for electrical insulation, and a steroid-eluting matrix may be included on or near the device to minimize fibrotic reaction, as is known in conventional pacing electrode-leads.

LPs 102 and 104 can utilize implant-to-implant (i2i) communication through event messages to coordinate operation with one another in various manners. The terms i2i communication, i2i event messages, and i2i even markers are used interchangeably herein to refer to event related messages and IMD/IMD operation related messages transmitted from an implanted device and directed to another implanted device (although external devices, e.g., a programmer, may also receive i2i event messages). In certain embodiments, LP 102 and LP 104 operate as two independent leadless pacers maintaining beat-to-beat dual-chamber functionality via a "Master/Slave" operational configuration. For descriptive purposes, the ventricular LP 104 shall be referred to as "vLP" and the atrial LP 102 shall be referred to as "aLP". LP 102, 104 that is designated as the master device (e.g. vLP) may implement all or most dual-chamber diagnostic and therapy determination algorithms. For purposes of the following illustration, it is assumed that the vLP is a "master" device, while the aLP is a "slave" device. Alternatively, the aLP may be designated as the master device, while the vLP may be designated as the slave device. The master device orchestrates most or all decision-making and timing determinations (including, for example, rate-response changes).

In accordance with certain embodiments, methods are provided for coordinating operation between first and second leadless pacemakers (LPs) configured to be implanted entirely within first and second chambers of the heart. A method transmits an event marker through conductive communication through electrodes located along a housing of the first LP, the event marker indicative of one of a local paced or sensed event. The method detects, over a sensing channel, the event marker at the second LP. The method identifies the event marker at the second LP based on a predetermined pattern configured to indicate that an event of interest has occurred in a remote chamber. In response to the identifying operation, the method initiates a related action in the second LP.

Optionally, wherein the first LP is located in an atrium and the second LP is located in a ventricle, the first LP produces an AS/AP event marker to indicate that an atrial sensed (AS) event or atrial paced (AP) event has occurred or will occur in the immediate future. For example, the AS and AP event markers may be transmitted following the corresponding AS or AP event. Alternatively, the first LP may transmit the AP event marker slightly prior to delivering an atrial pacing pulse. Alternatively, wherein the first LP is located in an atrium and the second LP is located in a ventricle, the second LP initiates an atrioventricular (AV) interval after receiving an AS or AP event marker from the first LP; and initiates a post atrial ventricular blanking (PAVB) interval after receiving an AP event marker from the first LP.

Optionally, the first and second LPs may operate in a "pure" master/slave relation, where the master LP delivers "command" markers in addition to or in place of "event" markers. A command marker directs the slave LP to perform an action such as to deliver a pacing pulse and the like. For example, when a slave LP is located in an atrium and a master LP is located in a ventricle, in a pure master/slave relation, the slave LP delivers an immediate pacing pulse to the atrium when receiving an AP command marker from the master LP.

In accordance with some embodiments, communication and synchronization between the aLP and vLP is implemented via conductive communication of markers/commands in the event messages (per i2i communication protocol). As explained above, conductive communication represents event messages transmitted from the sensing/pacing electrodes at frequencies outside the RF or Wi-Fi frequency range.

In an embodiment, ventricular-based pace and sense functionalities are not dependent on any i2i communication, in order to provide safer therapy. For example, in the event that LP to LP (i2i) communication is lost (prolonged or transient), the system 100 may automatically revert to safe ventricular-based pace/sense functionalities as the vLP device is running all of the necessary algorithms to independently achieve these functionalities. For example, the vLP may revert to a VVI mode as the vLP does not depend on i2i communication to perform ventricular pace/sense activities. Once i2i communication is restored, the system 100 can automatically resume dual-chamber functionalities.

Exemplary Communication Pathways Between External Programmer and LPs

Figure 4A:
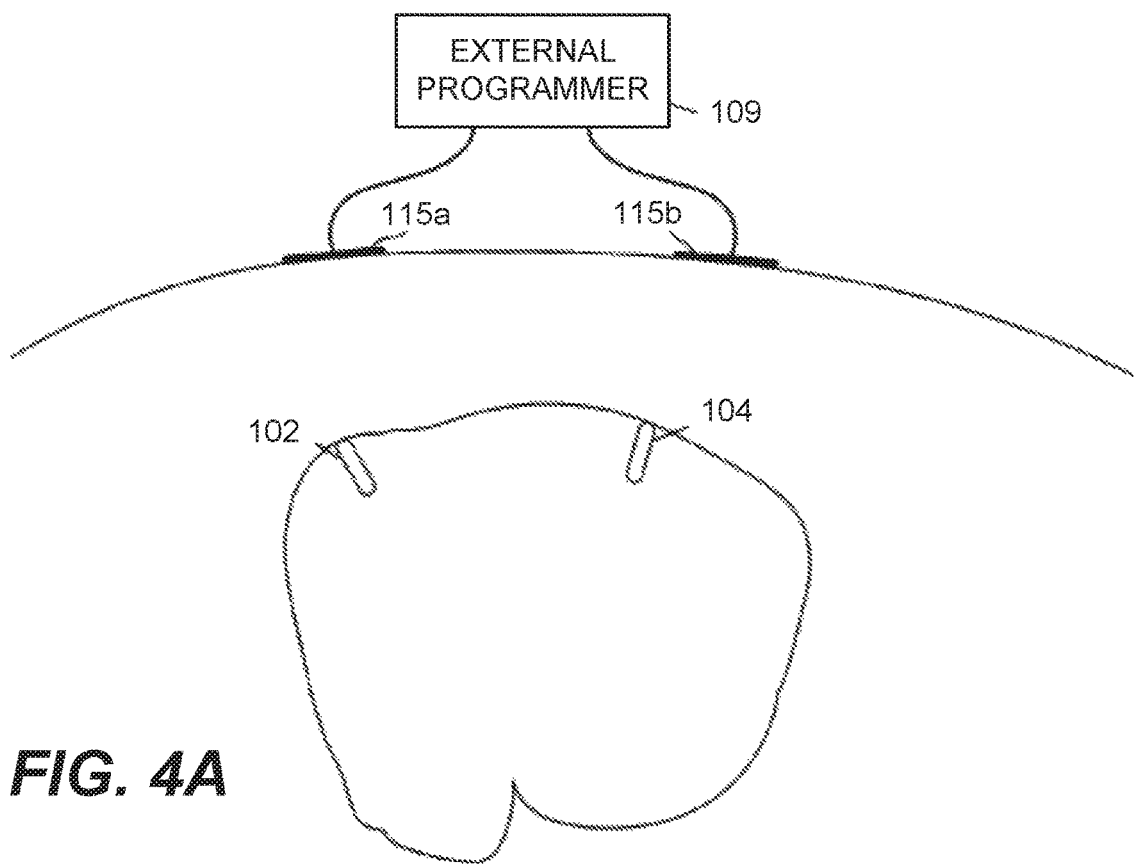
FIG. 4A depicts a sample configuration involving an external programmer and two endocardially implanted LPs.
Figure 4B:
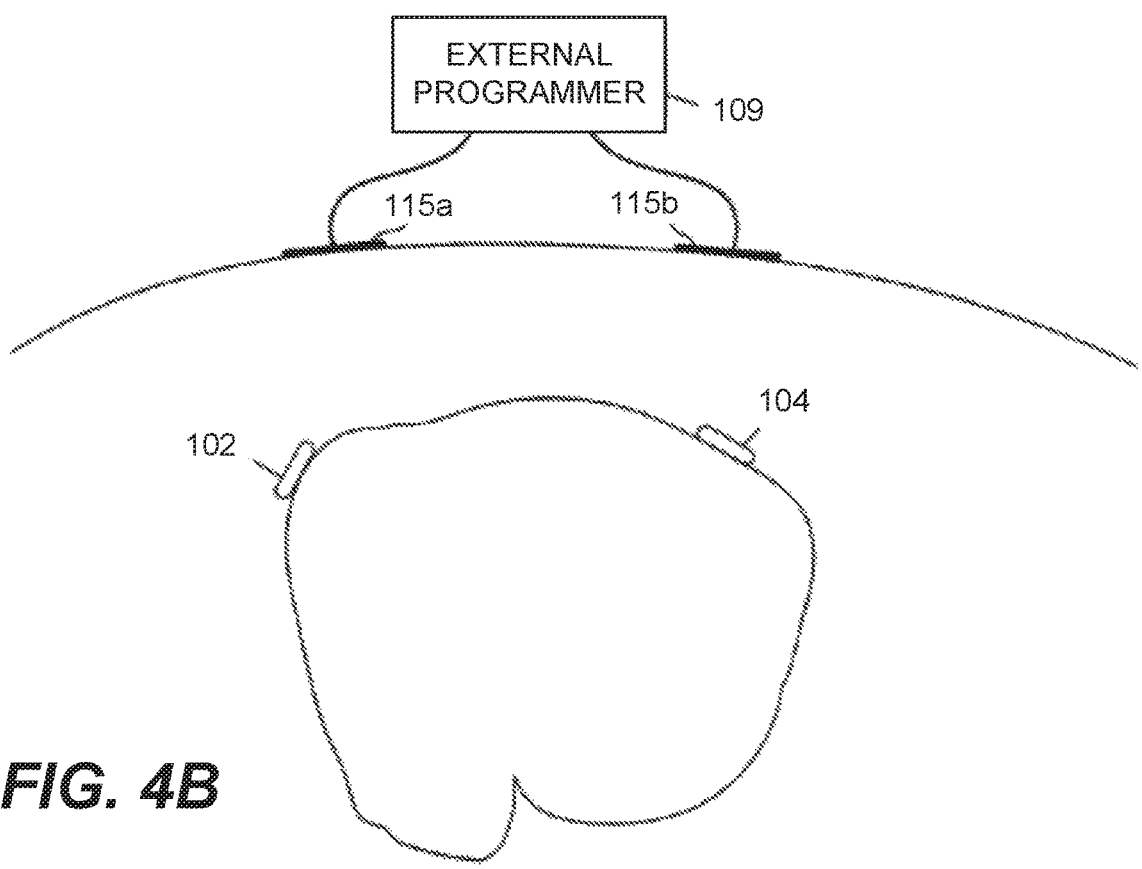
FIG. 4B depicts a sample configuration involving an external programmer and two LPs implanted epicardially (on the external heart surface).

FIGS. 4A and 4B are schematic pictorial views depicting how the external programmer can communicate with the LPs 102 and 104, or more generally with one or more IMDs, via conductive communication. Such communication may take place via bidirectional communication pathways comprising a receiving pathway that decodes information encoded on stimulation pulses generated by one or more of the implantable devices 102 or 104 and conductive through body tissue to the external programmer 109. According to the illustrative arrangement, the bidirectional communication pathways can be configured for communication with multiple LPs 102 and 104 via two or more electrodes 108a and 108b and conduction through body tissue.

In accordance with certain embodiments, the external programmer 109 is connected by a communication transmission channel and has transmitting and receiving functional elements for a bidirectional exchange of information with one or more IMDs, such as LP 102 and/or LP 104. The communication channel includes two or more programmer skin electrodes which can be affixed or secured to the surface of the skin. From the point of the skin, the communication transmission channel is wireless, includes the ion medium of the intra- and extra-cellular body liquids, and enables electrolytic-galvanic coupling between the programmer skin electrodes, which can also be referred to as surface electrodes, and the LPs, or more generally, IMDs. The bidirectional communication pathways can further comprise a transmitting pathway that passes information from the external programmer 109 to one or more of the LPs 102 and/or 104, or other IMD(s), by direct conduction through the body tissue by modulation that avoids skeletal muscle stimulation using modulated signals at a frequency in a range from approximately 10 kHz to 100 kHz, or at higher frequencies. For example, p2i communication signals may be transmitted at a center frequency ($f_c$) of 500 kHz.

Information transmitted from the external programmer 109 to the implanted LPs or other IMDs is conveyed by modulated signals at the approximate range of 10 kHz to 100 kHz which is a medium-high frequency, or at higher frequencies. The signals are passed through the communication transmission channel by direct conduction. A modulated signal in the frequency range has a sufficiently high frequency to avoid any depolarization within the living body which would lead to activation of the skeletal muscles and discomfort to the patient. The frequency is also low enough to avoid causing problems with radiation, crosstalk, and excessive attenuation by body tissue. Thus, information may be communicated at any time, without regard to the heart cycle or other bodily processes. No restriction is imposed regarding location of electrode placement on the body because low signal attenuation enables the signal to travel throughout the body and to be received by the IMD(s), e.g., LPs 102 and 104.

In some embodiments, the bidirectional communication pathways can further comprise a receiving pathway including a low-pass filter adapted to separate an electrocardiogram (ECG) from the information signals. The same surface electrodes 115 (also referred to as programmer skin electrode 115) that are used to transmit the information through the communication channel may also be used to detect a patient's electrocardiogram. Electrocardiogram frequencies are generally between 1 and 100 Hz, far lower than the 10 kHz to 100 kHz or higher range of frequencies used to transmit information through the communication transmission channel. Therefore, the electrocardiogram can be separated from the information signal by a low-pass filter and can optionally be displayed by the external programmer 109. In addition to low-pass filtering, blanking techniques that are typical in processing of cardiac signals can be used when the communication channel is active to prevent noise or erroneous signals from the communication channel affecting the electrocardiogram channel.

Because a plurality of LPs and/or other IMDs can be present, communication of information from the programmer is detected by all devices, enabling information to be sent to each implanted device without sending the same information multiple times.

In various embodiments and applications, the bidirectional communication pathways can further comprise a transmitting pathway that passes information from the programmer 109 to the one or more LPs and/or other IMDs in a common communication event whereby information is sent to one or more target devices of the IMDs using a selected technique. For example, information specific to a single IMD or a subset of IMDs having a unique address can be assigned to the single IMD or the subset of IMDs and encoded in the information. In another technique, information can designate a specific function that is executed by a particular IMD or a particular subset of IMDs. The information is passed to one or more IMDs without sending individual address information for activating execution by the particular IMD or the particular subset of IMDs alone. In another technique, information can designate a specific function that is executed by a particular IMD or a particular subset of IMDs that have programming specific to the function adapted to recognize the received information is relevant to the function.

Specifically, information that is specific to a single IMD or a subset of IMDs can be sent. A unique address can be assigned to each IMD or subset. The address can be encoded in the information sent to the plurality of IMDs, and any individual IMD can make use only of information that matches either the address or the address of the subset to which the particular IMD belongs.

In another technique, if each IMDs or subset of IMDs serves a specific function, which is different from other IMDs, then information may be passed to the specific IMD or subset without the additional overhead of a group or individual address.

In some embodiments, the one or more IMDs can comprise one or more LPs that generate cardiac pacing pulses and encode information onto the generated cardiac pacing pulses by selective alteration of pacing pulse morphology that is benign to therapeutic effect and energy cost of the pacing pulse. The cardiac pacing pulses conduct into body tissue via the electrodes for antenna-less and telemetry coil-less communication. For information transmitted from the LPs 102 and/and 104 to the external programmer 109, a communication scheme can be used in which the information is encoded on one or more pacing pulses. The pulse morphology is altered to contain the encoded information without altering the therapeutic benefits of the pacing pulse. The energy delivered by the pacing pulse remains essentially the same after the information is encoded. The external programmer 109 receives the pacing pulses through the associated surface electrodes 115. Encoded information is drawn from the pacing pulses and can contain state information of the implantable LP, such as battery voltage, lead impedance, sensed electrocardiogram amplitude, pacemaker current drain, programmed parameters, or other parameters.

The LPs 102 and/or 104 can be configured to detect a natural cardiac depolarization, time a selected delay interval, and deliver an information-encoded pulse during a refractory period following the natural cardiac depolarization. By encoding information in a pacing pulse, power consumed for transmitting information is not significantly greater than the power used for pacing. Information can be transmitted through the communication channel with no separate antenna or telemetry coil. Communication bandwidth is low with only a small number of bits encoded on each pulse.

In some embodiments, information can be encoded using a technique of gating the pacing pulse for very short periods of time at specific points in the pacing pulse. During the gated sections of the pulse, no current flows through the electrodes of an LP. Timing of the gated sections can be used to encode information. The specific length of a gated segment depends on the programmer's ability to detect the gated section. A certain amount of smoothing or low-pass filtering of the signal can be expected from capacitance inherent in the electrode/skin interface of the programmer as well as the electrode/tissue interface of the LP. A gated segment is set sufficiently long in duration to enable accurate detection by the programmer 109, limiting the amount of information that can be transmitted during a single pacing pulse. Accordingly, a technique for communication can comprise generating stimulation pulses on stimulating electrodes of an IMD and encoding information onto generated stimulation pulses. Encoding information onto the pulses can comprise gating the stimulation pulses for selected durations at selected timed sections in the stimulation pulses whereby gating removes current flow through the stimulating electrodes and timing of the gated sections encodes the information.

Another method of encoding information on pacing pulses involves varying the timing between consecutive pacing pulses in a pulse sequence. Pacing pulses, unless inhibited or triggered, occur at predetermined intervals. The interval between any two pulses can be varied slightly to impart information on the pulse series. The amount of information, in bits, is determined by the time resolution of the pulse shift. The steps of pulse shifting are generally on the order of microseconds. Shifting pulses by up to several milliseconds does not have an effect on the pacing therapy and cannot be sensed by the patient, yet significant information can be transmitted by varying pulse intervals within the microsecond range. The method of encoding information in variation of pulses is less effective if many of the pulses are inhibited or triggered. Accordingly, a technique for communication can comprise generating stimulation pulses on stimulating electrodes of an implanted biostimulator and encoding information onto generated stimulation pulses comprising selectively varying timing between consecutive stimulation pulses.

Alternatively or in addition to encoding information in gated sections and/or pulse interval, overall pacing pulse width can be used to encode information.

The exemplary described methods of encoding information on pacing pulses can use the external programmer 109 to distinguish pacing pulses from the patient's normal electrocardiogram, for example by recognition of the specific morphology of the pacing pulse compared to the R-wave generated during the cardiac cycle. For example, the external programmer 109 can be adapted to distinguish a generated cardiac pacing pulse from a natural cardiac depolarization in an electrocardiogram by performing comparative pattern recognition of a pacing pulse and an R-wave produced during a cardiac cycle.

The illustrative external programmer 109 and associated operating methods or techniques enable presentation to a user of information gathered from the LPs 102 and/or 104 and or other IMD(s) using conductive communication. Some of the information to be presented may include battery voltage, lead impedance, electrocardiogram amplitude, or current drain of the device. The information can be presented in addition to other information such as parameters to be set and programmed into the LP. The information can be presented to a user on a display screen. Some embodiments or configurations of an external programmer 109 can include a secondary link, for example either wireless or through a cable, to another display device, such as a handheld computer or terminal. The secondary link can also include communication over a local area network or the internet for display at a remote terminal.

FIG. 4A depicts a sample configuration involving the external programmer 109 and two endocardially implanted LPs 102 and 104. The external programmer 109 is physically connected to the skin surface via two programmer skin electrodes 115a and 115b (also referred to as surface electrodes), which can serve three functions. The programmer skin electrodes 115a and 115b can be referred to individually as a programmer skin electrode 115 (or a surface electrode 115), or collectively as programmer skin electrodes 115 (or surface electrodes 115). First, the electrodes 115 can be used transmit encoded information from the programmer 109 to the LPs or other IMD(s) using a modulated signal at a medium frequency 10 kHz to 100 kHz. Second, the programmer skin electrodes 115 can be used to receive information from individual LPs or other IMD(s) by detecting encoded information in the pacing pulses of the LP(s). Third, the programmer skin electrodes 115 can receive or sense a surface electrocardiogram for display and analysis by the programmer 109.

In FIG. 4A, the two LPs 102 and 104 are implanted endocardially. Alternatively, as shown in FIG. 4B, the two LPs 102 and 104 can be implanted by affixing to the exterior surface of the heart. The programmer skin electrodes 115 and the external programmer 109 function similarly in arrangements shown in FIGS. 4A and 4B whether the LPs 102 and 104 are implanted endocardially or epicardially (on the external heart surface). No restriction is imposed that the LPs are all implanted inside or all implanted outside the heart. One or more may be implanted endocardially along with others implanted on the outer surface of the heart. The functioning of the programmer 109 is substantially the same. Although two programmer skin electrodes 115 are shown in FIGS. 4A and 4B, two is generally the minimum number of programmer skin electrodes required for adequate conductive communication. More programmer skin electrodes 115 can be used, enabling an ECG to be sensed at multiple vectors for better analysis. More than two programmer skin electrodes may also enable a choice of vectors for conductive communication with the LPs, thereby maximizing the signal to noise ratio of the system. FIGS. 4A and 4B each depict two LPs 102 and 104. One, two, or more LPs can be implanted, depending on the number of pacemakers appropriate for effective therapy.

In various embodiments, the external programmer 109 can be configured to perform one or more operations such as electrocardiogram sensing, retrieving status information from implanted pacemakers, modifying configuration parameters of multiple implanted pacemakers simultaneously in information passed through a common electrode set, displaying electrocardiograms, displaying information received from the at least one implantable device, and others.

In various embodiments, an LP can manage power consumption to draw limited power from an internal battery, thereby reducing device volume. Each circuit in the LP can be designed to avoid large peak currents. For example, cardiac pacing can be achieved by discharging a tank capacitor (not shown) across the pacing electrodes. Recharging of the tank capacitor is typically controlled by a charge pump circuit. In a particular embodiment, the charge pump circuit can be throttled to recharge the tank capacitor at constant power from the battery. The one or more LPs can be configured to charge the tank capacitor in preparation for stimulation pulse generation, time one or more windows between pulse generation, disable charging of the tank capacitor during the one or more timed windows, and enable a receive amplifier in the implanted biostimulator while the tank capacitor is disabled.

In some embodiments, the external programmer 109 can detect a stimulation pulse from an LP and transmit data after a selected delay to coincide with a window that the LP's receiving amplifier is enabled.

The LP(s) and/or other IMD(s) can encode and/or decode information using various techniques such as encoding the information using pacing pulse width, binary-coded notches in a pacing pulse, modulation of off-time between pacing pulses, or other suitable encoding techniques. The external programmer 109 can encode and/or decode information using on-off keying encoding and modulation techniques. However, any other appropriate method can be used whereby a modulated bit-stream can be generated at a medium high frequency, for example frequency-shift keying, frequency modulation, or amplitude shift keying.

Exemplary External Programmer

Figure 5:
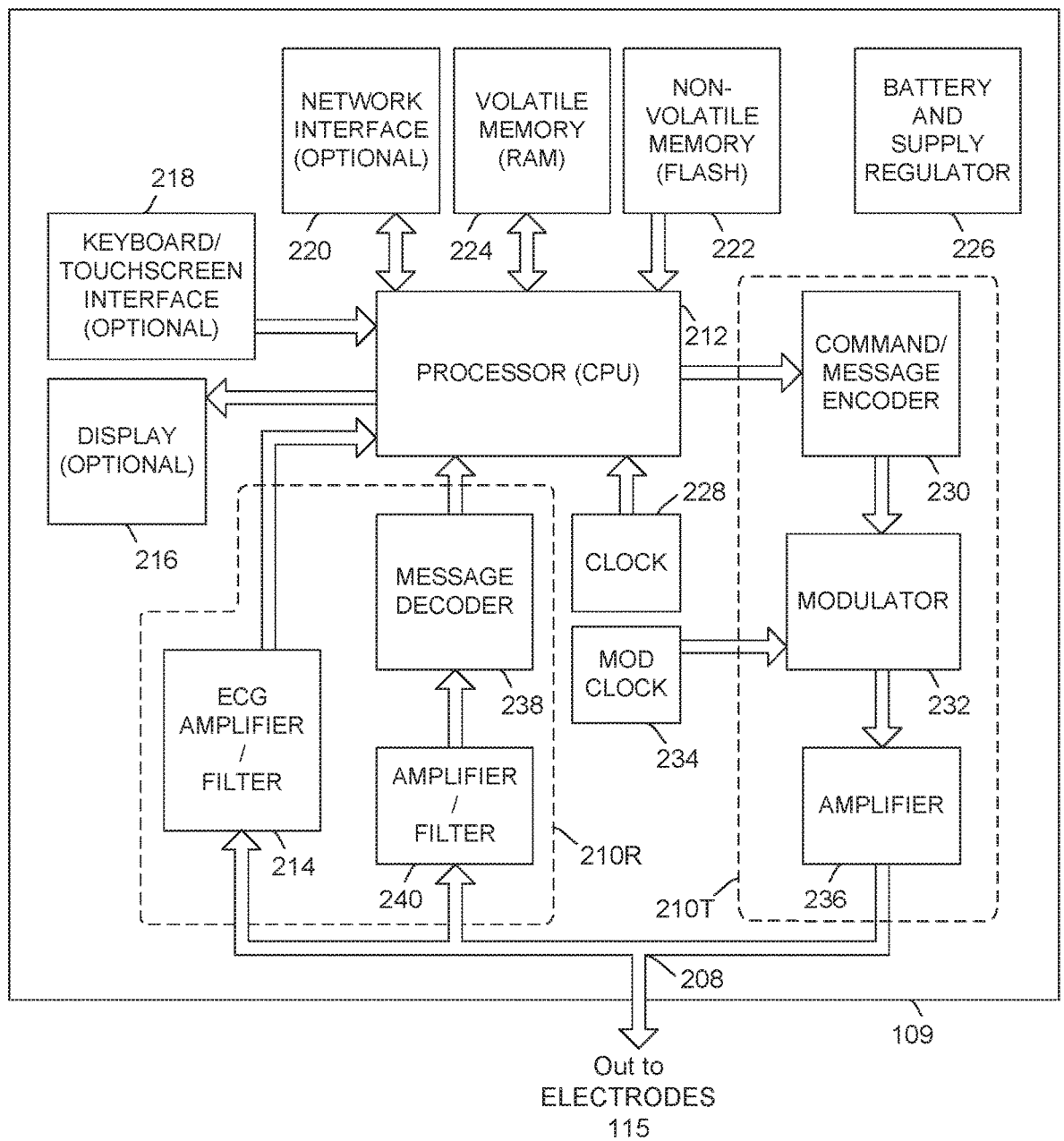
FIG. 5 is a schematic block diagram shows an embodiment of an external programmer adapted for communicating with one or more LPs and/or other IMD(s) using conductive communication.

Referring to FIG. 5, a schematic block diagram shows an embodiment of an external programmer 109 adapted for communicating with one or more LPs and/or other IMD(s) using conductive communication. The external programmer 109 comprises an interface 208 configured for coupling to at least two programmer skin electrodes 115 that make electrical contact with body skin for communicating with one or more IMDs. The external programmer 109 further comprises bidirectional communication pathways 210R and 210T coupled to the interface 208 and configured for bidirectional communication with the one or more IMDs. The communication pathways comprise a receiving pathway 210R that decodes information encoded on stimulation pulses generated by the one or more IMDs and conducted through body tissue.

The bidirectional communication pathways 210R and 210T are configured for communication with one or more LPs or other IMDs via the programmer skin electrodes 115 and conduction through body tissue.

The external programmer 109 can have bidirectional communication pathways 210R and 210T that further comprise a transmitting pathway 210T that passes information from the programmer 109 to one or more IMDs by conduction through the body tissue using modulation that avoids skeletal muscle stimulation.

In some arrangements, the bidirectional communication pathways 210R and 210T can be further specified to comprise a transmitting pathway that passes information from the programmer 109 to the one or more IMDs by direct conduction using modulated signals at a frequency in a range from approximately 10 kHz to 100 kHz, or at high frequencies, e.g., greater than 200 kHz. Also in some arrangements, the two or more programmer skin electrodes 115 and the bidirectional communication pathways 210R and 210T can be configured for bidirectional information signal communication and for sensing an electrocardiogram.

Also in some embodiments, the bidirectional communication pathways 210R and 210T can further comprise a transmitting pathway 210T that passes information from the programmer 109 to multiple IMDs in a common communication event. In some embodiments or selected operating conditions, the transmitting pathway 210T can be arranged to pass information from the programmer 109 to multiple IMDs in a common communication event whereby information specific to a single IMD or a subset of IMDs have a unique address assigned to the single IMD or the subset of IMDs and encoded in the information. The transmitting pathway 210T can also be arranged to pass information from the programmer 109 to multiple IMDs in a common communication event whereby information designates a specific function that is executed by a particular IMD or a particular subset of IMDs.

In the illustrative embodiment, the bidirectional communication pathways 210R and 210T comprise the two or more programmer skin electrodes 115 forming a conductive communication path between the programmer 109 and the skin surface, and a transmitting pathway 210T. The transmitting pathway 210T comprises a processor 212, a command/message encoder 230, a modulator 232, and an amplifier 236. The processor 212 is configured to communicate information to one or more LPs and/or other IMDs. The command/message encoder 230 is coupled to the processor 212 via a parallel interface and configured to encode and serialize data into a bit stream. Information encoding can be selected from encoding techniques such as on-off keying, frequency-shift keying, frequency modulation, and amplitude shift keying. The modulator 232 is coupled to the command/message encoder 230 and receives and modulates the serialized data using a frequency in a range from approximately 10 kHz to approximately 100 kHz. The amplifier 236 is coupled to the modulator 232 and increases signal amplitude to a level suitable for robust conductive communication.

The bidirectional communication pathways 210R and 210T further comprise a receiving pathway 210R including a low-pass filter 214 adapted to separate the electrocardiogram from the information signals.

In various embodiments and arrangements, the bidirectional communication pathways 210R and 210T further comprise a receiving pathway 210R that receives information at the programmer 109 from the one or more implanted biostimulators by conduction through the body tissue. The receiving pathway 210R can decode information, for example by decoding data that is encoded by the biostimulators using pacing pulse width, using binary-coded notches in a pacing pulse, using modulation of off-time between pacing pulses, or other suitable techniques for encoding data in the biostimulators.

In the illustrative embodiment, the bidirectional communication pathways 210R and 210T couple to the two or more programmer skin electrodes 115 forming a conductive communication path between the programmer 109 and the skin surface, and a receiving pathway 210R. The receiving pathway 210R comprises an electrocardiogram (ECG) amplifier/filter 214, an analog-to-digital converter (ADC) which is not shown in FIG. 5, and the processor 212. The electrocardiogram (ECG) amplifier/filter 214 includes a differential band-pass amplifier configured to select and amplify signals in a frequency range from approximately 1 Hz to approximately 100 Hz. The analog-to-digital converter (ADC) is configured to digitize the filtered and amplified signal. The processor 212 is coupled to the ADC and configured to receive and optionally display ECG data, and configured to decode information encoded into cardiac pacing pulses.

The programmer 109 may further comprise a processor 212 coupled to the bidirectional communication pathways and configured to manage communication with one or more IMDs, for example LPs. LPs can be implanted adjacent to an inside or an outside wall of a cardiac chamber as depicted in FIGS. 4A and 4B.

As depicted in FIG. 5, external programmer skin electrodes 115 enable a conductive communication path between the programmer 109 and the skin surface. Electrocardiogram (ECG) signals enter an ECG amplifier/filter 214, which can include a differential band-pass amplifier. In general, an ECG signal has spectral components in a range between 1 Hz and 100 Hz, and more generally, below 1 kHz. Band-pass filter poles for the ECG amplifier/filter 214 can be selected such that sufficient signal energy is passed within the 1 Hz to 100 Hz range, while filtering other signals that are not associated with cardiac activity. The ECG signal can be amplified and digitized using an analog-to-digital converter (ADC). Once digitized, the signal is passed to the processor, for example central processing unit (CPU) 212.

In some embodiments, the programmer skin electrodes 115 can be implemented with more than two electrodes to enable an electrocardiogram (ECG) to be sensed at multiple vectors and further to enable selection from among the multiple vectors for conductive communication with implanted LPs so that system signal-to-noise ratio can be improved or maximized.

The CPU 212 receives and optionally displays ECG data using a display interface 216 and can also display other data acquired from the implanted LPs acquired through the encoded pacing pulses, such as battery voltage, lead impedance, sensed cardiac signal amplitude, or other system status information. The CPU 212 also can accept input from a user via a keyboard and/or touch-screen interface 218. Some examples of user input are selected pacing rate or pacing pulse amplitude for implanted LPs. The CPU 212 can also communicate over a network interface 220 to other data entry or display units, such as a handheld computer or laptop/desktop unit. The network interface 220 can be cabled or wireless and can also enable communication to a local area network or the internet for greater connectivity.

The processor 212 is coupled to the bidirectional communication pathways and configured to perform one or more of various operations such as electrocardiogram sensing, retrieving status information from implanted LP(s) and/or other IMD(s), modifying configuration parameters thereof within a single or multiple cardiac cycles in information passed through a common electrode set, and other operations. A display interface 216 coupled to the processor 212 can be configured to display an electrocardiogram sensed from the programmer skin electrode 115. In some arrangements or embodiments, a secondary link 220 can be coupled to the processor 212 and configured for unidirectional or bidirectional wireless or cable transmission to and/or from a remote display and/or data-entry device to display an electrocardiogram sensed from the at least two electrodes, and/or to control the programmer and/or at least one IMD.

The CPU 212 can execute operations based on firmware stored in non-volatile memory (Flash) 222. The non-volatile memory 222 can also be used to store parameters or values that are to be maintained when power is removed. The CPU 212 uses volatile memory or random access memory (RAM) 224 as general storage for information such as ECG data, status information, swap memory, and other data. A battery and supply regulator 226 gives a constant voltage supply to the programmer 109 during normal operation. A clock module 228 generates a system clock signal used by the CPU 212 and by interface blocks for timing.

The CPU 212, during operation to communicate information to one or more implanted LPs, sends the information over a parallel interface to a command/message encoder 230, which serializes the data into a bit stream. Serialized data is sent to a modulator 232. The serialized bit-stream is modulated, for example using a frequency between 10 kHz and 100 kHz. An optional separate modulator clock 234 supplies a timing signal at a selected carrier frequency that may be used by the modulator 232. An amplifier 236 sets signal amplitude to a level that enables robust conductive communication. A sample of a modulated bit-steam is shown in FIG. 3 wherein logic high is shown as a medium high frequency sine wave. An encoding and modulation technique depicted in FIG. 3 is on-off keying. However, any other appropriate method whereby a modulated bit-stream can be generated at a medium high frequency may be used, for example frequency shift keying, frequency modulation, or amplitude shift keying.

Because multiple IMDs can be implanted, communication of information from the programmer 109 can be detected by all devices, enabling information to be sent to each IMD without sending the same information multiple times.

To reduce the peak current for operation of the LPs, a technique can be used in which a window or multiple windows occur between subsequent pacing pulses during which the LP does not charge pacing tank capacitor in preparation for the next pacing pulse. Instead the LP enables an internal receiving amplifier. Because the programmer 109 can sense pacing pulses from the IMDs, the programmer 109 can time data transmission to coincide with the pre-defined synchronous window or windows. A reduced peak current capability occurs because the charger and receiving amplifier, both power intensive elements, never have to be operated together. Because the data transmission is generally very short compared to the period between pacing pulses, the window technique should not significantly lower the ability of the LP to charge the pacing tank capacitor effectively between pacing pulses.

Referring again to FIG. 5, data acquired by the programmer 109 from a specific LP or other IMD is received at the programmer skin electrodes 115 and passes to an amplifier/filter 240, which functions to remove noise from the incoming signal. Any filtering performed by the amplifier/filter 240 is designed to leave encoded pulses intact as much as possible. A message decoder 238 determines whether the received signal is actually a pacing pulse or another signal, such as a cardiac R-wave.

Improving Conductive Communication Between External Programmer and IMD(s)

One potential problem with using conductive communication is that the orientation of the LP(s) and/or other IMD(s), relative to the programmer skin electrodes 115 that are used for conductive communication, can cause fading that adversely affects both programmer-to-implant (p2i) communication and implant-to-programmer (i2p) communication. More specifically, certain orientations of an LP or other IMD, relative to the programmer skin electrodes 115 that are used for conductive communication, may cause conductive communication to be intermittent or stop completely, which may occur when an electric potential field generated by the programmer skin electrodes 115 (e.g., generated by the electrodes 115a and 115b) has too small a difference between the receiving electrodes of the IMD (e.g., between the electrodes 108a and 108b of the LP 102 or 104). It is often impractical to mitigate such fading by changing the orientation of an IMD and/or the placement of its electrodes, since the orientation of the IMD and/or the placement of its electrodes is already severely constrained by mechanical and i2i communication requirements. Further, where the programmer skin electrodes 115 are also being used to sense an ECG, which is often the case, it is impractical to mitigate such fading by changing the placement of the programmer skin electrodes since the placement of such electrodes is often fixed or at least constrained by ECG requirements.

Embodiments of the present technology can be used to improve conductive communication between an external programmer (e.g., 109) and one or more IMDs, such as an LP 102 and/or 104, that is/are implanted within a patient. Such embodiments can be used to improve both p2i conductive communication, and i2p conductive communication. To avoid redundancy, the below discussion will mainly focus on the p2i conductive communication, since both p2i and i2p conductive communication experience fading under the approximately the same conditions according to the reciprocity theorem. More precisely, the fading conditions are substantially the same, if both p2i and i2p communication share the same narrow communication band and the same transmitting/receiving electrodes band. Further, the fading conditions are similar if the signal propagation is similar between i2p and p2i communication bands, and the external programmer's transmitting electrodes are placed closely to its receiving electrodes (or if the same programmer skin electrodes are used for transmitting and receiving). In certain embodiments, the external programmer utilizes a different pair of programmer skin electrodes for transmitting conductive communication signals than it does for receiving conductive communication signals, but either of the two electrodes used for transmitting can be paired with an electrode nearby that is used for receiving, and the pairs can be separated by a much larger distance from each other than the electrodes within each of the two pairs.

Figure 6:
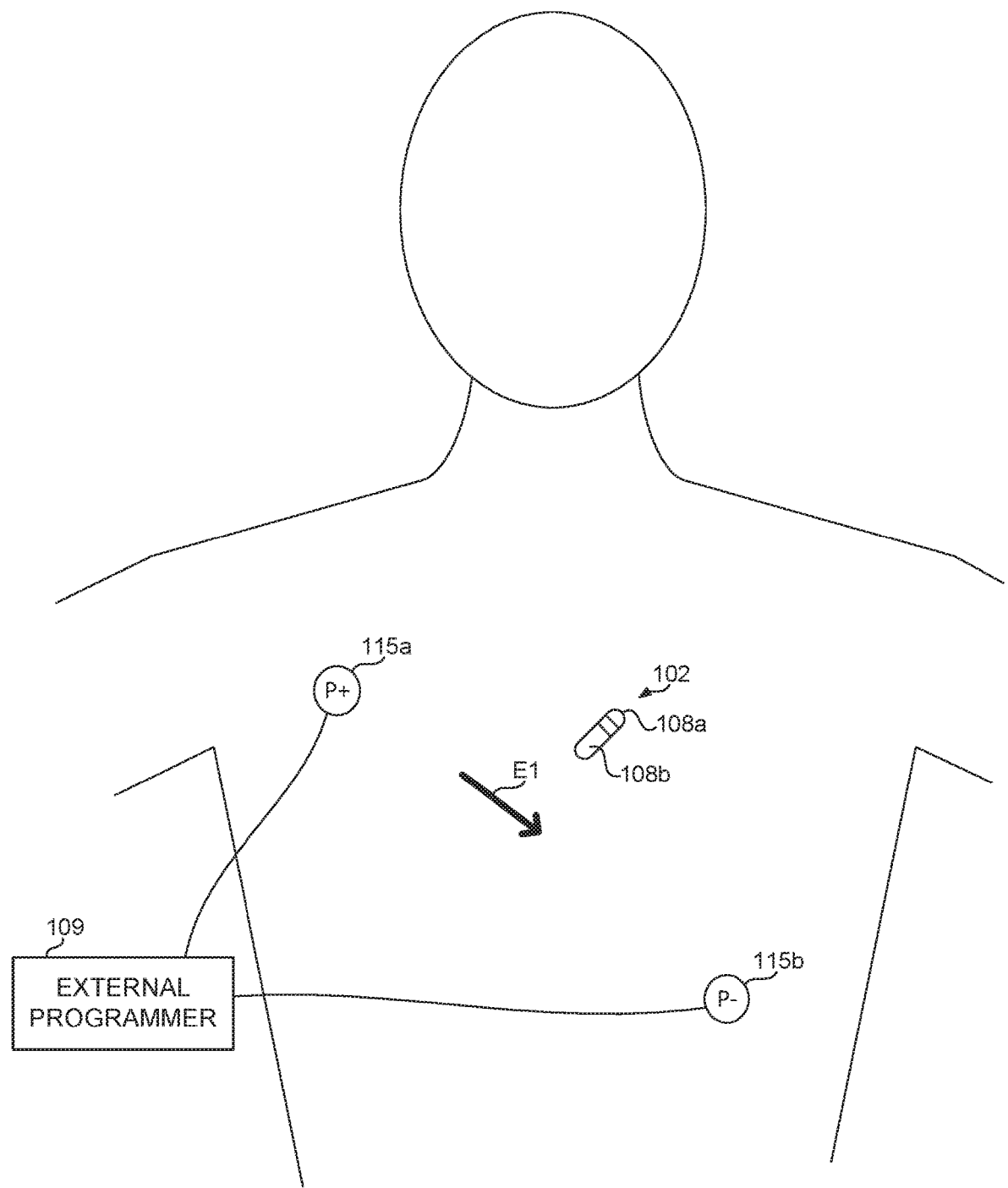
FIG. 6 is used to explain a typical fading situation that may cause conductive communication between an external programmer and one or more LPs and/or other IMD(s) to fail.

A typical fading situation will now be explained with reference to FIG. 6. Referring to FIG. 6, an external programmer 109 is shown as including or being coupled to a pair of programmer skin electrodes 115a and 115b that are attached to the skin of the torso of a patient in whom an LP 102 is implanted. The programmer skin electrode 115a and 115b are also labeled P+ and P− respectively, but could have been alternatively labeled P1 and P2. The programmer skin electrodes 115a and 115b can be referred to herein individually as a programmer skin electrode 115, or collectively as programmer skin electrodes 115.

FIG. 6 shows a representation of a primary electric field vector E1 (represented as a thick arrow) generated by and between the programmer skin electrode 115a and 115b. The implanted LP 102 is shown as including electrodes 108a and 108b, which are located relatively close to one another, and thus, form a dipole. As was explained above, the electrodes 108a and 108b can be used for both pacing and sensing, as well as for performing conductive communication. The electrodes 108a and 108b can be referred to individually as an electrode 108 or a leadless electrode 108, or collectively as electrodes 108 or leadless electrodes 108.

When the programmer skin electrodes 115a and 115b are used to transmit information to the LP 102 via conduction through body tissue, the voltage received by dipole of the LP 102 is proportional to the parallel component of the electric field vector E1, and more specifically, is the product of this parallel component and the effective dipole length of LP electrode dipole. As a result, even for a maximum dipole length of a few centimeters (e.g., if one the electrodes 108a of the LP 102 comprises coated sides of the LP housing, e.g., 202), the received voltage can drop well below the 1 mV level, and more generally, below a receiver sensitivity threshold. This can cause communication fading that results in lost p2i communication, as well as lost i2p communication.

Figure 7:
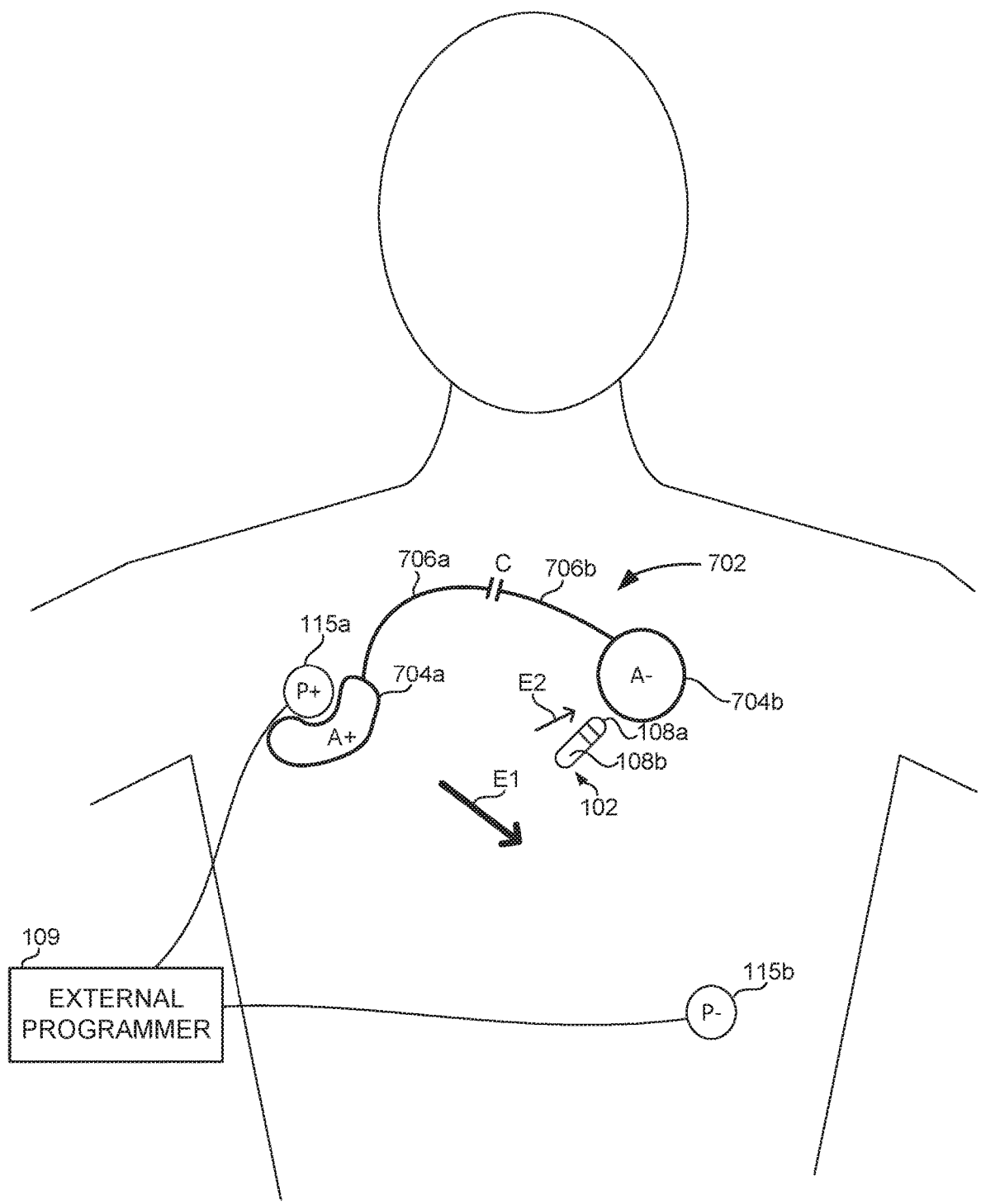
FIG. 7 is used to describe how an auxiliary apparatus, according to an embodiment of the present technology, can be used to improve conductive communication between an external programmer and an LP and/or other IMD.

Certain embodiments of the present technology, which will initially be described with reference to FIG. 7, are related to apparatuses and methods that improve conductive communication between an external programmer (e.g., 109) and an IMD (such as an LP 102) that is implanted within a patient. More specifically, certain embodiments of the present technology are related to an auxiliary apparatus that improves conductive communication between an external programmer and an IMD that is implanted within a patient. An embodiment of such an auxiliary apparatus is shown in FIG. 7.

Referring to FIG. 7, an auxiliary apparatus 702 according to an embodiment of the present technology is shown as including a first auxiliary skin electrode 704a, a second auxiliary skin electrode 704b and an electrically conductive path extending between the first and second auxiliary skin electrodes 704a and 704b and interrupted by a capacitor C. Each of the auxiliary skin electrodes 704a and 704b is configured to attach to skin of a patient. The auxiliary skin electrodes 704a and 704b, which can be referred to individually as an auxiliary skin electrode 704, or collectively as auxiliary skin electrodes 704, can each include a sticker or self-adhesive pad that can be used to adhere the auxiliary skin electrode 704 to a patient's skin. It is also possible that a gel or other type of adhesive be applied to the auxiliary skin electrodes 704 to enable them to be attached to the skin of a patient. The auxiliary skin electrodes 704 can also include an electrically conductive electrolyte gel that includes potassium chloride and/or silver chloride, to permit electron conduction from the skin to wires attached to the electrodes 704. Other variations are also possible, and within the scope of the embodiments described herein.

Still referring to FIG. 7, the capacitor C includes a pair of terminals, which can be referred to as a first terminal and a second terminal. In accordance with an embodiment, the electrically conductive path includes first and second electrically conductive wires 706a and 706b each having respective first and second ends. One end of the first electrically conductive wire 706a is connected to the first auxiliary skin electrode 704a and the other end of the electrically conductive wire 706a is connected to one of the terminals of the capacitor C. One end of the second electrically conductive wire 706b is connected to the second auxiliary skin electrode 704b and the other end of the electrically conductive wire 706b is connected to the other one of the terminals of the capacitor C.

As will be explained in additional detail below, the auxiliary apparatus 702 modifies a direction of the electric field vector generated between the programmer skin electrodes 115a and 115b to thereby improve the conductive communication between the external programmer 109 and the LP 102, and/or some other IMD. As will also be explained in additional detail below, the auxiliary apparatus 702 preferably causes a phase shift in communication signals that travel via conduction through body tissue and thereby reduces a probability and a depth of fading that may occur in p2i and i2p communication signals that travel via conduction through body tissue.

Where the auxiliary apparatus 702 only includes passive components, such as a capacitor, the surface area of each of the auxiliary skin electrodes 704 is preferably significantly larger than the typical surface area of each programmer skin electrode 115. For example, if the surface area of a programmer skin electrode 115 is approximately 1 cm$^2$, then each auxiliary skin electrode 704 preferably has a surface area of at least 10 cm$^2$, which is an order of magnitude greater than the approximately 1 cm$^2$ surface area of a programmer skin electrode 115. Preferably, the surface area of each of the auxiliary skin electrodes 704 is at least 20 cm$^2$, and may be significantly larger than that. A benefit of the auxiliary skin electrodes 704 being relatively large is that the larger the surface area of the auxiliary skin electrodes, the more the auxiliary device should be able to modify the direction of the electric field vector generated between the programmer skin electrodes 115.

While only two programmer skin electrodes 115 are shown as being attached to the skin of the patient in FIGS. 6 and 7, it is likely that at least five programmer skin electrodes 115 may be attached to the skin of the patient. In such a configuration, a first pair of the programmer skin electrodes can be used for transmitting conductive communication signals to one or more implanted LP(s) and/or other IMD(s), a second pair of the programmer skin electrodes can be used for receiving conductive communication signals from one or more implanted LP(s) and/or other IMD(s), and a fifth programmer skin electrode may function as a ground or common-mode electrode. All of the five (or more) programmer skin electrodes can be used for sensing an ECG signal. Because up to five or more programmer skin electrode 115 may be attached to the skin of a patient, this limits how large each of the auxiliary skin electrodes 704 can be. In accordance with certain embodiments, a maximum surface area of each of the auxiliary skin electrodes is 70 cm$^2$. In other words, in accordance with certain embodiments of the present technology, the surface area of each of the auxiliary skin electrodes is within the range of 20 cm$^2$ to 70 cm$^2$.

The auxiliary skin electrodes 704a and 704b can have various different shapes (i.e., peripheral geometries). For example, each of the auxiliary skin 704 electrodes can be circular, oval, tear drop shaped, square, rectangular, and/or the like. Both of the auxiliary skin electrodes 704a and 704b can have the same shape, or the auxiliary skin electrodes 704 may have shapes that differ from one another, e.g., as shown in FIG. 7. To provide for the most beneficial modification of the direction of the electric field vector generated between the programmer skin electrodes 115a and 115b, one of the auxiliary skin electrodes 704 should be placed as close as possible to one of the programmer skin electrodes 115, and the other auxiliary skin electrode 704 should be placed generally proximate to a skin location below which an LP or other IMD is implanted within the patient. The programmer skin electrodes 115 are typically circular in shape. In order to enable one of the auxiliary skin electrodes 704 (e.g., 704a in FIG. 7) to be located as close as possible to one of the programmer skin electrodes (e.g., 115a in FIG. 7), at least one of the auxiliary skin electrodes (e.g., 704a in FIG. 7) can have a kidney bean shape or crescent shape, as shown in FIG. 7. The other auxiliary skin electrode 704 (e.g., 704b in FIG. 7) can have a circular shape, but is not limited thereto.

In FIG. 7, the auxiliary skin electrode 704a is labeled A+ because it is located next to the programmer skin electrode 115a labeled P+, and the auxiliary skin electrode 704b is labeled A− because it is located closer than the auxiliary skin electrode 704a to the programmer skin electrode 115b labeled P−. However, it is noted that were the auxiliary apparatus 702 only includes passive components, as is the case in FIG. 7, there is no actual electrical distinction between the auxiliary skin electrodes 704 labeled A+ and A−, other than their placement relative to the programmer skin electrodes 115.

Still referring to FIG. 7, the electrically conductive path between the auxiliary skin electrode 704a and 704b provides a low impedance path therebetween. When the external programmer 109 transmits a conductive communication signal using the programmer skin electrode 115a and 115b, a voltage potential difference is created between the programmer skin electrodes 115a and 115b. This voltage potential difference induces a current in the electrically conductive path between the auxiliary skin electrodes 704a and 704b, which path is interrupted by the capacitor C. This current induces a secondary electric field E2 (represented as a thin arrow), which can have a sufficiently large component parallel to the dipole of the LP provided by the electrodes 108a and 108b of the LP (and/or other IMD).

In FIG. 7, the secondary electric field E2 is shown as being generally parallel to the dipole of the LP provided by the electrodes 108a and 108b of the LP (or other IMD). However, it is noted that the goal of improving communication between the external programmer 109 and the LP 102 (and/or other IMD) will still be achieved where the secondary electric field vector E2 is not parallel to the dipole, so long as there is a significantly strong electric field component (caused by a vector combination of the electric field vectors E1 and E2) parallel to the dipole provided by the electrodes 108a and 108b.

Sufficiently large auxiliary skin electrodes 704 are beneficial to achieve a significant anti-fading effect due to their decreased contact impedance. Such low contact impedance is beneficial, because the primary electric field potential caused by the programmer skin electrodes 115 drops very quickly as the distance from the programmer skin electrodes 115 increases. As a result, a primary-field-induced potential drops quickly with the distance from the closest programmer skin electrode 115, and an open-circuit voltage between the auxiliary skin electrode 704a and 704b may only be on the order of ~100 mV (even under the optimal placement of auxiliary skin electrodes 704, where one of them is very close to one of the programmer skin electrodes 115). In other words, it is beneficial to provide a sufficiently small contact spreading impedance between the patient's body and each of the auxiliary skin electrodes 704, so that a "short-circuit" current between the pair of auxiliary skin electrodes 704 creates a sufficiently large secondary electric field vector E2 at the location of the dipole of the LP or other IMD.

Both theory and in-saline experiments have demonstrated that with properly placed and connected auxiliary skin electrodes, deep fade in p2i and i2p communication can be eliminated. In such experiments, circular shaped auxiliary skin electrodes having a radius of 3 cm (and thus, a surface area of ~28 cm$^2$) were used. In saline tank measurements, the parallel secondary field at the dipole of an LP exceeded 22% of the total primary field at the location of the dipole of the LP. In other words, received signal strength was restored from almost zero to more than one fifth of its maximum value (i.e. the would-be value for the best LP orientation parallel to the primary electric field vector).

In the embodiment of FIG. 7, a simple passive circuit including only the capacitor C and the electrically conductive wires 706a and 706b is connected between the auxiliary skin electrodes 704a and 704b. In accordance with an embodiment, the value of the capacitor C is chosen sufficiently low to minimize the inter-electrode current through the capacitor at ECG frequencies, which are below 1 kHz, but sufficiently high not to seriously hamper the inter-electrode current at communication frequencies, which are typically higher than 200 kHz. In the in-saline experiments, the value of the capacitor C was 0.01 µF, with a reactance is above 1.5 kΩ (kilo-ohms) at frequencies below 1 kHz, and below 8 Ω at frequencies above 200 kHz. The former reactance value was more than sufficiently high to have no effect on sensed ECG signals, while the latter was much lower than the through-body impedance between the auxiliary skin electrodes 704a and 704b above 200 kHz. In the in-saline experiments, it was assumed that the impedance of body tissue between the auxiliary skin electrodes (which impedance can be represented by $R_{a2a}$) was about 50Ω. With these values, the capacitor C is essentially an open circuit at ECG frequencies and a short circuit at communication frequencies.

A somewhat lower value of the connecting capacitor C may be beneficial, so that a significant phase shift occurs between the secondary current between the auxiliary skin electrodes 704 and a would-be open-circuit voltage between the auxiliary skin electrodes 704. To achieve such a phase shift without significantly reducing the secondary current, the reactance of the connecting capacitor C should be roughly equal the impedance of the body tissue between the auxiliary skin electrodes at communication frequencies (in absolute value). As an example, for a communication band centered at $f_c$=500 kHz and $R_{a2a}$=50Ω, the value of the capacitor C~$1/(2*pi*f_c*R_{a2a})$=6.37 nF, with C=6.8 nF being a good standard capacitance value. Other values for the capacitor C would also work, and it is believed that this value can be increased by up to 200%, or reduced by up to 70%, while still providing for satisfactory improvement in p2i and i2p communication. In other words, the value for the capacitor C can be within a range from approximately $0.3*(1/(2\pi*f_c*R_{a2a}))$ to $3.0*\{1/(2\pi*f_c*R_{a2a})\}$, wherein C is a value of the capacitor, $f_c$ is a center frequency of a communication band used for the conductive communication between the external programmer and the IMD, and $R_{a2a}$ is an impedance of the body tissue between the auxiliary skin electrodes. Assuming $f_c$=500 KHz, and $R_{a2a}$=50 ohms, then the capacitor C can have a value within the range from approximately 2 nF to 13 nF.

Beneficially providing the aforementioned phase shift in the secondary current provides for a large reduction in the probability and depth of fading, even for random implant orientations. In fact, with significant phase shift, deep fading should only occur in the very unlikely situation that an electrode dipole formed by the electrodes 108a and 108b of the LP, or other IMD, is essentially perpendicular to both the primary electric field E1 and the secondary electric field E2. Without the aforementioned phase shift, deep fading may occur where the electrode dipole formed by the electrodes 108a and 108b of the LP, or other IMD, is generally perpendicular to the vector sum of the primary and secondary electric fields (E1+E2), i.e. to the total electric field at LP or other IMD location. Therefore, properly decreasing of the value of connecting capacitor C for significant phase shift between the primary field and secondary current is more beneficial, if the fading implant orientation may change with time and spans a large angular range, or if multiple implants (e.g., LP 102 and LP 104) are prone to fading and are oriented quite differently. On the other hand, if the implant (s) hardly change their orientations over time, it may be easier to eliminate fading by choosing a higher value for the capacitor C, thereby maximizing the secondary current (at the expense of lower phase shift).

The effect of auxiliary skin electrodes 704 on the primary electric field vector E1 can be mentally pictured as follows. The programmer skin electrodes 115a and 115b transmit a primary in-body current. The auxiliary skin electrodes 704a and 704b try to collect and re-channel part of this current in order to achieve a more favorable-to-communicate (more parallel to the LP dipole) orientation of the total electric field at the LP location. To collect more current, it helps to place one of the auxiliary skin electrodes (e.g., 704a) close to one of the programmer skin electrodes (e.g., 115a), while the other auxiliary skin electrode goes somewhere where there is a significant open-circuit voltage difference between the auxiliary skin electrodes 704a and 704b relative to the primary electric field vector E1. It also helps to reduce the impedance between each auxiliary skin electrodes 704 and the patient's body, which is achieved by making the auxiliary skin electrodes 704 relatively large. To create a sufficiently strong secondary electric field vector E2 with favorable orientation at the dipole of the LP or other IMD, one of the auxiliary skin electrodes (e.g., 704b) is placed close to the LP or other IMD so that its contribution to the secondary electric field vector E2 will have a large enough component parallel to the dipole of the LP or other IMD, assuming that the other auxiliary skin electrode, e.g., 704a, is much farther from the LP or other IMD and therefore does not contribute much to the secondary electric field vector E2.

Figure 8:
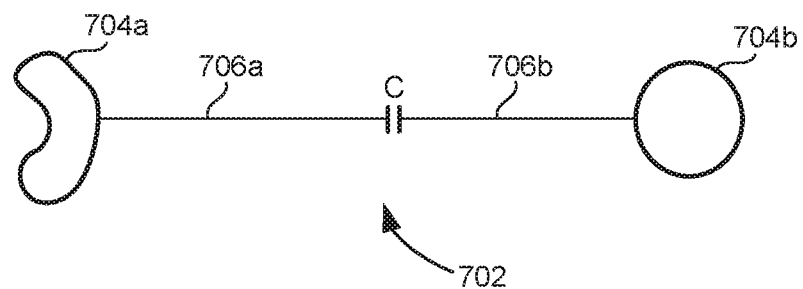
FIG. 8 is a simplified diagram illustrating the auxiliary apparatus introduced with reference to FIG. 7.

FIG. 8 is a simplified view of the auxiliary apparatus 702 initially described above with reference to FIG. 7. A benefit of the auxiliary apparatus 702, and the other auxiliary apparatuses of the present technology described below, is that they can improve the p2i and i2p communication between an external programmer (e.g., 109) and one or more IMDs without making any modifications to the hardware of the external programmer, without making any modifications to the hardware of the IMD(s), without making any modifications the firmware or software or the external programmer, and without making any modifications to the firmware or software of the IMD(s). Indeed, the external programmer and the IMD(s) will be totally unaware of the presence of the auxiliary apparatus 702. Thus, in the event that a physician or clinician is having difficulty effecting conductive communication between an external programmer and one or more IMDs, the physician or clinician may attach an auxiliary apparatus of the present technology to the patient's skin, to improve p2i and i2p conductive communication. Such auxiliary apparatuses may be sold and stored within a sterile pouch, or the like, with instructions for how to use the auxiliary apparatus printed on the pouch or other package, or included within the pouch or other package.

In the embodiments shown in FIGS. 7 and 8, the capacitor C of the auxiliary apparatus 702 passes frequencies within a first frequency band used for the conductive communication between an external programmer and one or more IMD(s), and the capacitor C attenuates frequencies within a second frequency band that is lower than the first frequency band and in which cardiac electrical activity occurs. Accordingly, the capacitor C of the auxiliary apparatus 702 does not adversely affect the external programmer's ability to sense electrocardiogram signals using at least two programmer skin electrodes (e.g., 115). The first frequency band can be, e.g., from 450 KHz to 550 KHz, but is not limited thereto. The frequency content of electrocardiogram signals are much lower, and more specifically, are below 1 KHz.

Figure 9:
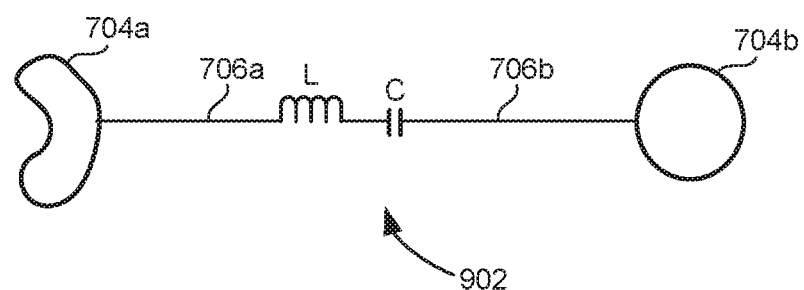
FIG. 9 is a diagram illustrating an auxiliary apparatus according to another embodiment of the present technology.

FIG. 9 shows an auxiliary apparatus 902, according to an alternative embodiment of the present technology. Components that are the same in FIG. 9, as they are in FIGS. 7 and 8 described above are labeled the same and need not be described again. A comparison between the auxiliary apparatus 902 and the auxiliary apparatus 702 shows that the auxiliary apparatus 902 adds an inductor L in series with the capacitor C to form a series resonant LC band-pass filter. The series resonant LC band-pass filter is configured to pass a first frequency band used for the conductive communication between an external programmer and one or more IMD(s), and to attenuate frequencies outside of the first frequency band. An exemplary first frequency band used for conductive communication is 450 KHz to 550 KHz, but is not limited thereto.

Figure 10:
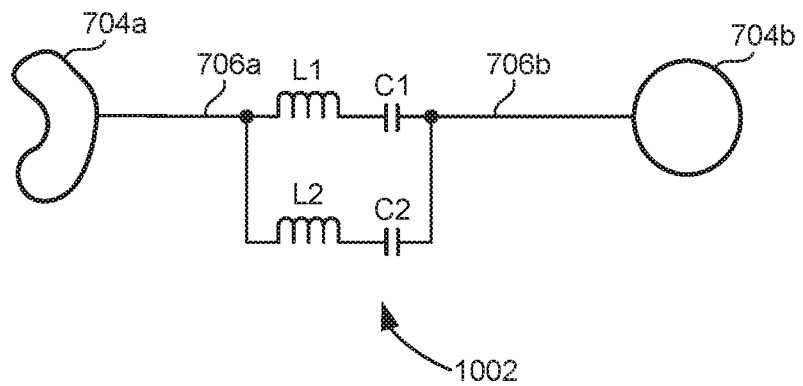
FIG. 10 is a diagram illustrating an auxiliary apparatus according to a further embodiment of the present technology.

FIG. 10 shows an auxiliary apparatus 1002, according to another embodiment of the present technology, which includes a first series resonant LC band-pass filter (include a capacitor C1 and an inductor L1) and a second series resonant LC band-pass filter (include a capacitor C2 and an inductor L2) that are connected in parallel with one another. The first series resonant LC band-pass filter can be configured to pass a first frequency band used for p2i conductive communication between an external programmer and one or more IMD(s), and to attenuate frequencies outside of the first frequency band. The second series resonant LC band-pass filter can configured to pass a second frequency band used for i2p conductive communication between one or more IMD(s) and an external programmer, and to attenuate frequencies outside of the second frequency band. Thus the combined effect of both LC band-pass filters (which can also be referred to as LC tanks) is to selectively pass currents in the first and second frequency bands and at least partially block currents at frequencies out of these bands.

In the embodiments of the present technology described above with reference to FIGS. 7-10, the auxiliary apparatuses only include passive elements, and thus, do not require a power supply and therefore can be made relatively inexpensively. In alternative embodiments, which are somewhat more complex, an auxiliary apparatus can also include one more active components. For example, an auxiliary apparatus according to an embodiment of the present technology can include an amplifier, a filter and a feedback canceller, and potentially also a delay line. Where an amplifier, which is an active component, is included in the auxiliary apparatus, the auxiliary skin electrodes can be made smaller than they could otherwise be made if the auxiliary apparatus only included passive components. This is because of the gain that can be provided by an amplifier. An auxiliary apparatus that includes one or more active components can include its own power supply, such as a battery, or can be connected to an external power supply, depending upon implementation. Depending upon implementation, an auxiliary apparatus that includes one or more active components may include up to four auxiliary skin electrodes, or just two auxiliary skin electrodes.

Figure 11:
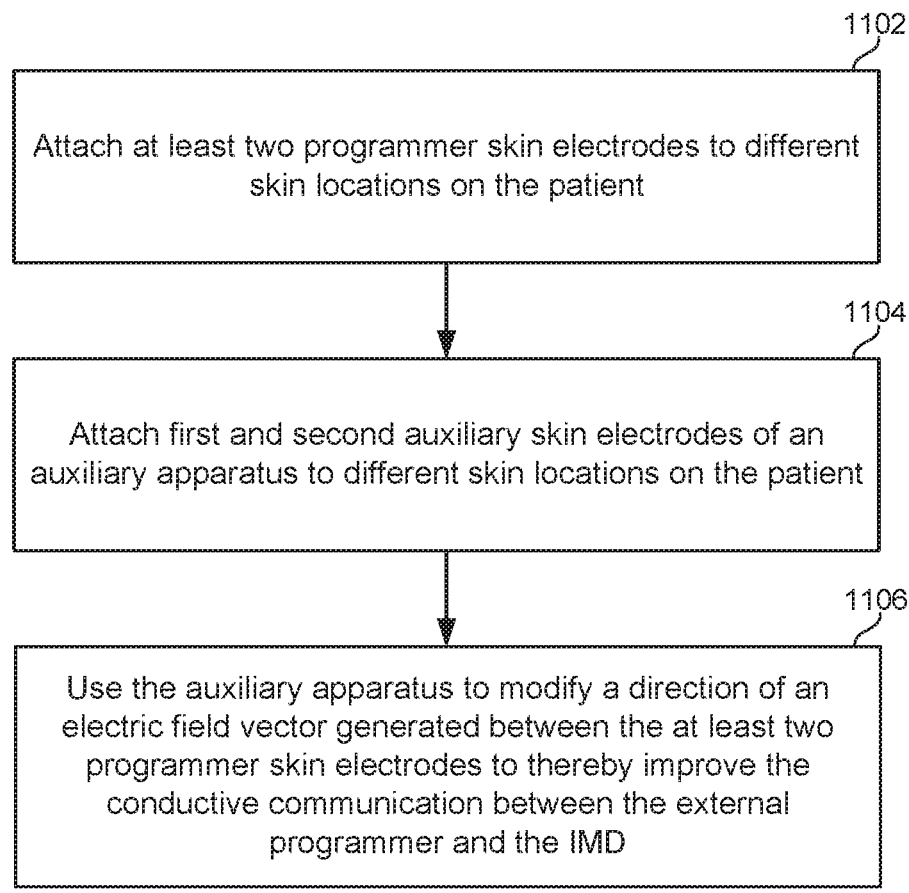
FIG. 11 is a high level flow diagram that is used to summarize methods of improving conductive communication between an external programmer and one or more IMDs in accordance with various embodiments of the present technology.

FIG. 11 is a high level flow diagram that is used to summarize methods according to certain embodiments of the present technology. Such methods can be used for improving conductive communication between an external programmer and one or more IMD(s) that is/are implanted within a patient, wherein the IMD includes or is coupled to at least two implantable electrodes (e.g., 108a and 108b) that enable the IMD to at least one of transmit information to or receive information from the external programmer via conduction through body tissue of the patient. The electrodes (e.g., 108a and 108b) of the IMD can also be used for pacing and/or sensing, as explained above.

Referring to FIG. 11, step 1102 involves attaching at least two programmer skin electrodes to different skin locations on the patient, wherein the at least two programmer skin electrodes are part of or electrically coupled to the external programmer. Step 1104 involves attaching first and second auxiliary skin electrodes of an auxiliary apparatus to different skin locations on the patient, wherein the auxiliary apparatus also includes an electrically conductive path extending between the first and second auxiliary skin electrodes and interrupted by a capacitor, and wherein the auxiliary apparatus is distinct from the external programmer and the IMD(s). Step 1102 can be performed prior to step 1104, or alternative, step 1104 can be performed before step 1102. Still referring to FIG. 11, step 1106 involves using the auxiliary apparatus to modify a direction of an electric field vector generated between the at least two programmer skin electrodes to thereby improve the conductive communication between the external programmer and the IMD.

Additionally, a method can also include using the auxiliary apparatus to cause a phase shift in communication signals that travel via conduction through body tissue of the patient and thereby reduce a probability and a depth of fading that may occur in the communication signals that travel via conduction through body tissue of the patient. Such a phase shift can be caused by selecting appropriate values of the capacitor(s) of the auxiliary apparatus, as was described above in more detail in the discussion of FIG. 7.

A method can also include using the capacitor to pass frequencies within a first frequency band used for the conductive communication between the external programmer and IMD, and using the capacitor to attenuate frequencies within a second frequency band that is lower than the first frequency band and in which cardiac electrical activity occurs, and thereby, not adversely affecting the external programmer's ability to sense electrocardiogram signals using the at least two programmer skin electrodes.

In accordance with an embodiment, step 1104 involves attaching one of the first and second auxiliary skin electrodes of the auxiliary apparatus proximate to, and more specifically, as close as possible to, one of the at least two programmer skin electrodes. Step 1104 can also involve attaching the other one of the first and second auxiliary skin electrodes generally proximate to a skin location below which the IMD is implanted. If communication between the external programmer and the IMD is not sufficiently improved, repositioning of one or both of the auxiliary skin electrodes can be attempted to see if that improves the p2i and/or i2p communication, in order to further optimize the direction of the secondary electric field. Further details of the methods summarized with reference to FIG. 11 can be appreciated from the above discussions of the auxiliary apparatuses with reference to FIGS. 7-10, as well as the discussion of the other FIGS.

Block Diagram of LP

Figure 12:
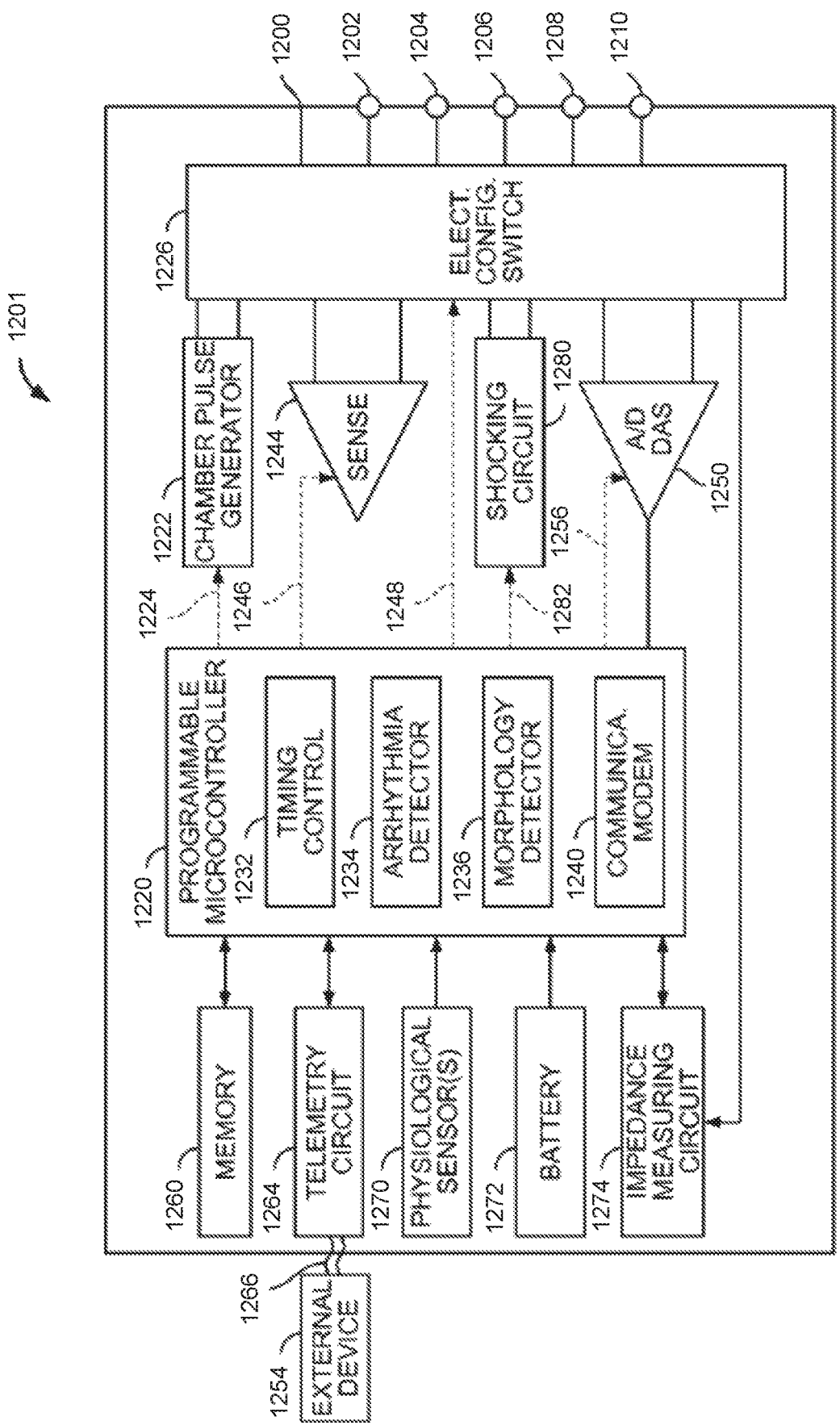
FIG. 12 shows a block diagram of one embodiment of an LP that is implanted within a patient as part of an implantable cardiac system.

FIG. 12 shows a block diagram that shows further details of one embodiment of an LP 1201 that is implanted into a patient as part of the implantable cardiac system in accordance with certain embodiments herein. The auxiliary apparatuses described above with reference to FIGS. 7-10, and the methods described above with reference to FIG. 11, can be used to improve the p2i and i2p conductive communication between an external programmer and the LP 1201. LP 1201 may be implemented as a full-function biventricular pacemaker, equipped with both atrial and ventricular sensing and pacing circuitry for four chamber sensing and stimulation therapy (including both pacing and shock treatment). Optionally, LP 1201 may provide full-function cardiac resynchronization therapy. Alternatively, LP 1201 may be implemented with a reduced set of functions and components. For instance, the IMD may be implemented without ventricular sensing and pacing. The LP 1201 can be, e.g., the LP 102 or 104. LP 1201 has a housing 1200 to hold the electronic/computing components.

Housing 1200 (which is often referred to as the "can", "case", "encasing", or "case electrode") may be programmably selected to act as the return electrode for certain stimulus modes. Housing 1200 may further include a connector (not shown) with a plurality of terminals 1202, 1204, 1206, 1208, and 1210. The terminals may be connected to electrodes that are located in various locations on housing 1200 or elsewhere within and about the heart. LP 1201 includes a programmable microcontroller 1220 that controls various operations of LP 1201, including cardiac monitoring and stimulation therapy. Microcontroller 1220 includes a microprocessor (or equivalent control circuitry), RAM and/or ROM memory, logic and timing circuitry, state machine circuitry, and I/O circuitry.

LP 1201 further includes a first pulse generator 1222 that generates stimulation pulses for delivery by one or more electrodes coupled thereto. Pulse generator 1222 is controlled by microcontroller 1220 via control signal 1224. Pulse generator 1222 may be coupled to the select electrode(s) via an electrode configuration switch 1226, which includes multiple switches for connecting the desired electrodes to the appropriate I/O circuits, thereby facilitating electrode programmability. Switch 1226 is controlled by a control signal 1248 from microcontroller 1220.

In the embodiment of FIG. 12, a single pulse generator 1222 is illustrated. Optionally, the IMD may include multiple pulse generators, similar to pulse generator 1222, where each pulse generator is coupled to one or more electrodes and controlled by microcontroller 1220 to deliver select stimulus pulse(s) to the corresponding one or more electrodes.

Microcontroller 1220 is illustrated as including timing control circuitry 1232 to control the timing of the stimulation pulses (e.g., pacing rate, atrio-ventricular (AV) delay, atrial interconduction (A-A) delay, or ventricular interconduction (V-V) delay, etc.). Timing control circuitry 1232 may also be used for the timing of refractory periods, blanking intervals, noise detection windows, evoked response windows, alert intervals, marker channel timing, and so on. Microcontroller 1220 also has an arrhythmia detector 1234 for detecting arrhythmia conditions and a morphology detector 1236. Although not shown, the microcontroller 1220 may further include other dedicated circuitry and/or firmware/software components that assist in monitoring various conditions of the patient's heart and managing pacing therapies.

LP 1201 is further equipped with a communication modem (modulator/demodulator) 1240 to enable wireless communication with the remote slave pacing unit. Modem 1240 may include one or more transmitters and two or more receivers as discussed herein in connection with FIG. 1. In one implementation, modem 1240 may use low or high frequency modulation. As one example, modem 1240 may transmit i2i messages and other signals through conductive communication between a pair of electrodes. Modem 1240 may be implemented in hardware as part of microcontroller 1220, or as software/firmware instructions programmed into and executed by microcontroller 1220. Alternatively, modem 1240 may reside separately from the microcontroller as a standalone component.

LP 1201 includes a sensing circuit 1244 selectively coupled to one or more electrodes, that perform sensing operations, through switch 1226 to detect the presence of cardiac activity in the right chambers of the heart. Sensing circuit 1244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The automatic gain control enables the unit to sense low amplitude signal characteristics of atrial fibrillation. Switch 1226 determines the sensing polarity of the cardiac signal by selectively closing the appropriate switches. In this way, the clinician may program the sensing polarity independent of the stimulation polarity.

The output of sensing circuit 1244 is connected to microcontroller 1220 which, in turn, triggers or inhibits the pulse generator 1222 in response to the presence or absence of cardiac activity. Sensing circuit 1244 receives a control signal 1246 from microcontroller 1220 for purposes of controlling the gain, threshold, polarization charge removal circuitry (not shown), and the timing of any blocking circuitry (not shown) coupled to the inputs of the sensing circuitry.

In the embodiment of FIG. 12, a single sensing circuit 1244 is illustrated. Optionally, the IMD may include multiple sensing circuits, similar to sensing circuit 1244, where each sensing circuit is coupled to one or more electrodes and controlled by microcontroller 1220 to sense electrical activity detected at the corresponding one or more electrodes. Sensing circuit 1244 may operate in a unipolar sensing configuration or in a bipolar sensing configuration.

LP 1201 further includes an analog-to-digital (A/D) data acquisition system (DAS) 1250 coupled to one or more electrodes via switch 1226 to sample cardiac signals across any pair of desired electrodes. Data acquisition system 1250 is configured to acquire intracardiac electrogram signals, convert the raw analog data into digital data, and store the digital data for later processing and/or telemetric transmission to an external device 1254 (e.g., a programmer, local transceiver, or a diagnostic system analyzer). Data acquisition system 1250 is controlled by a control signal 1256 from the microcontroller 1220. The external device 1254 can be, e.g., the external programmer 109 discussed above.

Microcontroller 1220 is coupled to a memory 1260 by a suitable data/address bus. The programmable operating parameters used by microcontroller 1220 are stored in memory 1260 and used to customize the operation of LP 1201 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of LP 1201 may be non-invasively programmed into memory 1260 through a telemetry circuit 1264 in telemetric communication via communication link 1266 with external device 1254. Telemetry circuit 1264 allows intracardiac electrograms and status information relating to the operation of LP 1201 (as contained in microcontroller 1220 or memory 1260) to be sent to external device 1254 through communication link 1266.

LP 1201 can further include magnet detection circuitry (not shown), coupled to microcontroller 1220, to detect when a magnet is placed over the unit. A magnet may be used by a clinician to perform various test functions of LP 1201 and/or to signal microcontroller 1220 that external device 1254 is in place to receive or transmit data to microcontroller 1220 through telemetry circuits 1264.

LP 1201 can further include one or more physiological sensors 1270. Such sensors are commonly referred to as "rate-responsive" sensors because they are typically used to adjust pacing stimulation rates according to the exercise state of the patient. However, physiological sensor 1270 may further be used to detect changes in cardiac output, changes in the physiological condition of the heart, or diurnal changes in activity (e.g., detecting sleep and wake states). Signals generated by physiological sensors 1270 are passed to microcontroller 1220 for analysis. Microcontroller 1220 responds by adjusting the various pacing parameters (such as rate, AV Delay, V-V Delay, etc.) at which the atrial and ventricular pacing pulses are administered. While shown as being included within LP 1201, physiological sensor(s) 1270 may be external to LP 1201, yet still be implanted within or carried by the patient. Examples of physiologic sensors might include sensors that, for example, sense respiration rate, pH of blood, ventricular gradient, activity, position/posture, minute ventilation (MV), and so forth.

A battery 1272 provides operating power to all of the components in LP 1201. Battery 1272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). Battery 1272 also desirably has a predictable discharge characteristic so that elective replacement time can be detected. As one example, LP 1201 employs lithium/silver vanadium oxide batteries.

LP 1201 further includes an impedance measuring circuit 1274, which can be used for many things, including: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves; and so forth. Impedance measuring circuit 1274 is coupled to switch 1226 so that any desired electrode may be used. In this embodiment LP 1201 further includes a shocking circuit 1280 coupled to microcontroller 1220 by a data/address bus 1282.

In some embodiments, the LPs are configured to be implantable in any chamber of the heart, namely either atrium (RA, LA) or either ventricle (RV, LV). Furthermore, for dual-chamber configurations, multiple LPs may be co-implanted (e.g., one in the RA and one in the RV, one in the RV and one in the coronary sinus proximate the LV). Certain pacemaker parameters and functions depend on (or assume) knowledge of the chamber in which the pacemaker is implanted (and thus with which the LP is interacting; e.g., pacing and/or sensing). Some non-limiting examples include: sensing sensitivity, an evoked response algorithm, use of AF suppression in a local chamber, blanking & refractory periods, etc. Accordingly, each LP needs to know an identity of the chamber in which the LP is implanted, and processes may be implemented to automatically identify a local chamber associated with each LP.

Processes for chamber identification may also be applied to subcutaneous pacemakers, ICDs, with leads and the like. A device with one or more implanted leads, identification and/or confirmation of the chamber into which the lead was implanted could be useful in several pertinent scenarios. For example, for a DR or CRT device, automatic identification and confirmation could mitigate against the possibility of the clinician inadvertently placing the V lead into the A port of the implantable medical device, and vice-versa. As another example, for an SR device, automatic identification of implanted chamber could enable the device and/or programmer to select and present the proper subset of pacing modes (e.g., AAI or VVI), and for the IPG to utilize the proper set of settings and algorithms (e.g., V-AutoCapture vs ACap-Confirm, sensing sensitivities, etc.).

While many of the embodiments of the present technology described above have been described as being for use with LP type IMDs, embodiments of the present technology that are for use in reducing how often a first receiver of an IMD wakes up a second receiver of an IMD, in order to reduce power consumption, can also be used with other types of IMDs besides an LP. Accordingly, unless specifically limited to use with an LP, the claims should not be limited to use with LP type IMDs.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, it is noted that the term "based on" as used herein, unless stated otherwise, should be interpreted as meaning based at least in part on, meaning there can be one or more additional factors upon which a decision or the like is made. For example, if a decision is based on the results of a comparison, that decision can also be based on one or more other factors in addition to being based on results of the comparison.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. An auxiliary apparatus that improves conductive communication between an external programmer and an implantable medical device (IMD) that is implanted within a patient, wherein
   the IMD includes or is coupled to at least two implantable electrodes that enable the IMD to at least one of transmit information to or receive information from the external programmer via conduction through body tissue of the patient,
   the external programmer includes or is coupled to at least two programmer skin electrodes that are configured to attach to skin of the patient and that enable the external programmer to at least one of transmit information to or receive information from the IMD via conduction through body tissue of the patient, and
   an electric field vector is generated between a pair of the at least two programmer skin electrodes when the external programmer uses the pair to transmit information to or receive information from the IMD via conduction through body tissue,
   the auxiliary apparatus comprising:
   a first auxiliary skin electrode configured to attach to skin of a patient;
   a second auxiliary skin electrode configured to attach to skin of a patient; and
   an electrically conductive path extending between the first and second auxiliary skin electrodes and interrupted by a capacitor;
   wherein the auxiliary apparatus is distinct from and not part of the external programmer and the IMD, and
   wherein the auxiliary apparatus is configurable to modify a direction of the electric field vector generated between the pair of the at least two programmer skin electrodes to thereby improve the conductive communication between the external programmer and the IMD.

2. The auxiliary apparatus of claim 1, wherein:
   the electrically conductive path extending between the first and second auxiliary skin electrodes provides a low impedance path therebetween,
   a voltage potential difference is generated between the pair of the at least two programmer skin electrodes when the external programmer uses the pair to transmit information to or receive information from the IMD via conduction through body tissue, the voltage potential difference induces a current in the electrically conductive path extending between the first and second auxiliary skin electrodes, which path is interrupted by the capacitor, and the current in the electrically conductive path extending between the first and second auxiliary skin electrodes induces a secondary electric field.

3. The auxiliary apparatus of claim 2, wherein:

the at least two implantable electrodes of the IMD form a dipole, and the secondary electric field is generally parallel to the dipole of the IMD.

4. The auxiliary apparatus of claim 2, wherein:

the at least two implantable electrodes of the IMD form a dipole, and a vector of the secondary electric field generated between the first and second auxiliary skin electrodes combines with the vector of the electric field generated between the pair of the at least two programmer skin electrodes to form a combined vector that is parallel to the dipole of the IMD.

5. The auxiliary apparatus of claim 1, wherein the auxiliary apparatus causes a phase shift in communication signals that travel via conduction through body tissue and thereby reduces a probability and a depth of fading that may occur in the communication signals that travel via conduction through body tissue.

6. The auxiliary apparatus of claim 1, wherein:

the capacitor includes a first terminal and a second terminal;

the electrically conductive path includes first and second electrically conductive wires each having respective first and second ends;

the first end of the first electrically conductive wire is connected to the first auxiliary skin electrode;

the first end of the second electrically conductive wire is connected to the second auxiliary skin electrode; and the capacitor is connected in series between the second ends of the first and second electrically conductive wires.

7. The auxiliary apparatus of claim 1, wherein:

the capacitor passes frequencies within a first frequency band used for the conductive communication between the external programmer and IMD; and the capacitor attenuates frequencies within a second frequency band that is lower than the first frequency band and in which cardiac electrical activity occurs, and thus, the capacitor of the auxiliary apparatus does not adversely affect the external programmer's ability to sense electrocardiogram signals using the at least two programmer skin electrodes.

8. The auxiliary apparatus of claim 1, further comprising: an inductor in series with the capacitor;

wherein the inductor and capacitor collectively provide a series resonant LC band-pass filter that is configured to pass electric currents in a first frequency band used for the conductive communication between the external programmer and IMD, and attenuate electric currents at frequencies outside of the first frequency band.

9. The auxiliary apparatus of claim 1, wherein C has a value within a range from $0.3*\{1/(2\pi*f_c*R_{a2a})\}$ to $3*\{1/(2\pi_c*R_{a2a})\}$, wherein C is a value of the capacitor, $f_c$ is a center frequency of a communication band used for the conductive communication between the external programmer and the IMD, and $R_{a2a}$ is an impedance of the body tissue between the auxiliary skin electrodes.

10. The auxiliary apparatus of claim 9, wherein:

$f_c$=500 kHz;

$R_{a2a}$ is assumed to be equal to 50 ohms; and

C has a value within the range from 2.00 nF to 12.74 nF.

11. The auxiliary apparatus of claim 1, wherein a surface area of each of the first and second auxiliary skin electrodes is at least 10 cm$^2$.

12. The auxiliary apparatus of claim 1, wherein the auxiliary apparatus does not include any active electrical components, and thus, does not require its own power supply.

13. The auxiliary apparatus of claim 1, wherein the auxiliary apparatus includes one or more active electrical components.

14. The auxiliary apparatus of claim 1, wherein a surface area of each of the first and second auxiliary skin electrodes is larger than the surface area of each of the programmer skin electrodes.

15. The auxiliary apparatus of claim 1, wherein a surface area of each of the first and second auxiliary skin electrodes is an order of magnitude greater than the surface area of each of the programmer skin electrodes.

16. A method for improving conductive communication between an external programmer and an implantable medical device (IMD) that is implanted within a patient, wherein the IMD includes or is coupled to at least two implantable electrodes that enable the IMD to at least one of transmit information to or receive information from the external programmer via conduction through body tissue of the patient, the method comprising:

attaching at least two programmer skin electrodes to different skin locations on the patient, wherein the at least two programmer skin electrodes are part of or electrically coupled to the external programmer;

attaching first and second auxiliary skin electrodes of an auxiliary apparatus to different skin locations on the patient, wherein the auxiliary apparatus also includes an electrically conductive path extending between the first and second auxiliary skin electrodes and interrupted by a capacitor, and wherein the auxiliary apparatus is distinct from and not part of the external programmer and the IMD; and using the auxiliary apparatus to modify a direction of an electric field vector generated between the at least two programmer skin electrodes to thereby improve the conductive communication between the external programmer and the IMD.

17. The method of claim 16, further comprising using the auxiliary apparatus to cause a phase shift in communication signals that travel via conduction through body tissue of the patient and thereby reduce a probability and a depth of fading that may occur in the communication signals that travel via conduction through body tissue of the patient.

18. The method of claim 16, further comprising:

using the capacitor to pass frequencies within a first frequency band used for the conductive communication between the external programmer and IMD; and using the capacitor to attenuate frequencies within a second frequency band that is lower than the first frequency band and in which cardiac electrical activity occurs, and thereby, not adversely affecting the external programmer's ability to sense electrocardiogram signals using the at least two programmer skin electrodes.

19. The method of claim 16, wherein the attaching the first and second auxiliary skin electrodes of the auxiliary apparatus to different skin locations on the patient comprises:
    attaching one of the first and second auxiliary skin electrodes of the auxiliary apparatus proximate to one of the at least two programmer skin electrodes; and
    attaching the other one of the first and second auxiliary skin electrodes generally proximate to a skin location below which the IMD is implanted.

20. The method of claim 16, wherein the auxiliary apparatus further comprises an inductor in series with the capacitor, the method further comprising:
    using a series resonant LC band-pass filter, which is collectively provided by the inductor and the capacitor of the auxiliary apparatus, to pass a first frequency band used for the conductive communication between the external programmer and IMD, and to attenuate frequencies outside of the first frequency band.

* * * * *